(12) United States Patent
Suzuki et al.

(10) Patent No.: US 8,702,701 B2
(45) Date of Patent: Apr. 22, 2014

(54) TREATMENT DEVICE FOR ELECTROSURGERY

(75) Inventors: Keita Suzuki, Tokyo (JP); Hideki Fujii, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/409,434

(22) Filed: Mar. 1, 2012

(65) Prior Publication Data

US 2012/0220993 A1 Aug. 30, 2012

Related U.S. Application Data

(63) Continuation of application No. PCT/JP2010/071985, filed on Dec. 8, 2010.

(30) Foreign Application Priority Data

Jan. 29, 2010 (JP) .................................. 2010-018130

(51) Int. Cl.
*A61B 18/14* (2006.01)

(52) U.S. Cl.
USPC .............................................. 606/48; 606/46

(58) Field of Classification Search
USPC ........ 606/29, 39, 41, 46, 48, 50, 171; 607/98, 607/99, 115
See application file for complete search history.

(56) References Cited

U.S. PATENT DOCUMENTS

| | | | |
|---|---|---|---|
| 3,986,212 A | 10/1976 | Sauer | |
| 4,311,143 A | 1/1982 | Komiya | |
| 5,843,019 A * | 12/1998 | Eggers et al. | 604/22 |
| 7,419,488 B2 * | 9/2008 | Ciarrocca et al. | 606/41 |
| 2004/0210215 A1 * | 10/2004 | Okada | 606/45 |

FOREIGN PATENT DOCUMENTS

| | | |
|---|---|---|
| EP | 1 042 990 A1 | 10/2000 |
| JP | 61-9061 B2 | 3/1986 |
| JP | 619051 B2 | 3/1986 |
| JP | 9-140723 A | 6/1997 |
| JP | 2000-185053 A | 7/2000 |

(Continued)

OTHER PUBLICATIONS

International Search Report PCT/JP2010/071985 dated Mar. 15, 2011.

(Continued)

*Primary Examiner* — Michael Peffley
*Assistant Examiner* — Thomas Giuliani
(74) *Attorney, Agent, or Firm* — Scully, Scott, Murphy & Presser, P.C.

(57) ABSTRACT

A treatment device for electrosurgery includes a sheath that has a distal end portion and a proximal end portion; a needle-like electrode that has a distal end and a proximal end, is inserted into the sheath such that it is capable of advancing and retracting inside the sheath, and treats a target site at the distal end; a first electrode provided at the distal end of the needle-like electrode and exposed from the sheath; a second electrode fixed with respect to the first electrode at a position separated from the first electrode toward the proximal end; an insulator that insulates the first electrode from the second electrode by being interposed between the first and second electrodes; a first conductive portion that applies a high-frequency current to the first electrode; and a second conductive portion that applies a high-frequency current to the second electrode.

8 Claims, 24 Drawing Sheets

(56) References Cited

FOREIGN PATENT DOCUMENTS

| | | |
|---|---|---|
| JP | 2002-514097 A | 5/2002 |
| JP | 2002-224135 A | 8/2002 |
| JP | 2004-167081 A | 6/2004 |
| JP | 2005-144142 A | 6/2005 |
| JP | 2006-512959 A | 4/2006 |
| JP | 2006-280662 A | 10/2006 |
| JP | 2007-535972 A | 12/2007 |
| JP | 2009-112794 A | 5/2009 |
| JP | 2009-254650 A | 11/2009 |
| WO | WO 2008/152674 A1 | 12/2008 |

OTHER PUBLICATIONS

Japanese Office Action dated Oct. 4, 2011 from corresponding Japanese Patent application No. JP 2011-532370.

Extended Supplementary European Search Report dated Oct. 7, 2013 from related European Application No. 10 844 700.4.

* cited by examiner

TREATMENT DEVICE FOR ELECTROSURGERY

FIELD OF THE INVENTION

The present invention relates to a treatment device for electrosurgery. This application is a continuation application based on a PCT Patent Application No. PCT/JP2010/071985, filed on Dec. 8, 2010, whose priority is claimed on Japanese Patent Application No. 2010-018130, filed Jan. 29, 2010. The contents of both the PCT Application and the Japanese Application are incorporated herein by reference.

BACKGROUND OF THE INVENTION

Description of the Related Art

Conventionally, in the medical field or the like, a treatment tool in which a treatment portion that treats a body tissue is provided to the distal end of an insertion portion inserted into a body cavity is known. Particularly, as a treatment tool that performs a surgical treatment, such as making an incision, on a body tissue, a treatment device for electrosurgery which cauterizes and incises a body tissue contacting a treatment portion by applying a high-frequency current to the treatment portion is known.

This type of treatment device for electrosurgery is broadly classified into a treatment device for so-called monopolar electrosurgery that includes a first electrode inserted into a body cavity and a second electrode disposed on the body surface, and a treatment device for so-called bipolar electrosurgery that includes first and second electrodes disposed in a body cavity.

For example, Japanese Unexamined Patent Application, First Publication No. 2002-224135 discloses a treatment device for bipolar electrosurgery. This treatment device for bipolar electrosurgery disclosed in Japanese Unexamined Patent Application, First Publication No. 2002-224135 includes an electrode (passive electrode) that is provided to the distal end portion of a catheter tube and an electrode (incision electrode) that is provided so as to be able to move in the catheter tube. According to this treatment device for bipolar electrosurgery, an opposite electrode (the second electrode described above) does not need to be provided outside the body of a patient, and it is possible to incise the body tissue while suppressing invasiveness to the body tissue.

In addition, Japanese Examined Patent Application, Second Publication No. S61-9051 discloses a high-frequency incision tool that incises a body tissue by using a snare applied with a high-frequency current. This high-frequency incision tool disclosed in Japanese Examined Patent Application, Second Publication No. S61-9061 includes a sheath that is formed of an outer tube and an inner tube having an electrical insulation property, an operation wire that is inserted into the sheath so as to freely move forward and backward and performs an operation for the forward and backward movement at the proximal side of the sheath, a snare (incision electrode) that is connected to the distal end of the operation wire, an electrode (passive electrode) that is fixed to the distal end of the sheath while being exposed and contacts a body tissue, and means for conductively connecting the electrodes and the snare to a high-frequency generating device through the inside of the sheath.

According to this high-frequency incision tool, a body tissue to be incised is gripped with the snare, and at this point in time, by causing a high-frequency current to flow, the body tissue can be cauterized.

SUMMARY OF THE INVENTION

According to a first aspect of present invention, a treatment device for electrosurgery includes a sheath that has a distal end portion and a proximal end portion, a treatment portion that has a distal end and a proximal end, is inserted into the sheath such that a direction toward the distal end portion from the proximal end portion becomes a direction toward the distal end from the proximal end, and treats a target site at the distal end, a first electrode that is provided to the distal end of the treatment portion and exposed to the outside, a second electrode of which the relative positional relationship with respect to the first electrode is fixed at a position separated from the first electrode toward the proximal end in the treatment portion, an insulator that insulates the first electrode from the second electrode by being interposed between the first and second electrodes, a first conductive portion that applies a high-frequency current to the first electrode, and a second conductive portion that applies a high-frequency current to the second electrode, wherein a plurality of electrodes, which become passive electrodes of the high-frequency current between the first electrode and the second electrode, is provided.

According to a second aspect of present invention, the first electrode is formed while bulging to the outside in the radial direction of the treatment portion so as to have a diameter greater than or equal to the external diameter of the second electrode.

According to a third aspect of present invention, the first electrode is formed in a semispherical shape of which the diameter decreases toward the distal end from the proximal end.

According to a fourth aspect of present invention, to the distal end of the second electrode, an extending portion that is formed while extending to the outside of the radial direction of the second electrode is provided.

According to a fifth aspect of present invention, an enlarged passive electrode that is provided to the outer surface of the distal end portion of the sheath and electrically connected to the first electrode is further included.

According to a sixth aspect of present invention, the treatment device for electrosurgery further includes an enlarged second electrode that is provided to the outer surface of the distal end portion of the sheath and electrically connected to the second electrode.

According to a seventh aspect of present invention, the sheath includes an electroconductive coil sheath in the inside thereof, and the coil sheath preferably functions as a portion of the second conductive portion.

According to an eighth aspect of present invention, the treatment device for electrosurgery further includes a second insulator that hides at least a portion of the outer surface of the second electrode so as to expose a portion of the distal end of the second electrode in the approximately the same area as the surface area of the first electrode.

According to a ninth aspect of present invention, the first electrode is a portion of a ring-like snare loop having electrical conductivity.

According to a tenth aspect of present invention, the first electrode is a pair of two-legged forceps having a pair of elastic gripping portions that extend in the distal end direction from the proximal end and can be opened and closed using the proximal end as a center of opening and closing.

DETAILS DESCRIPTION OF THE INVENTION (First Embodiment)

Figure 1:
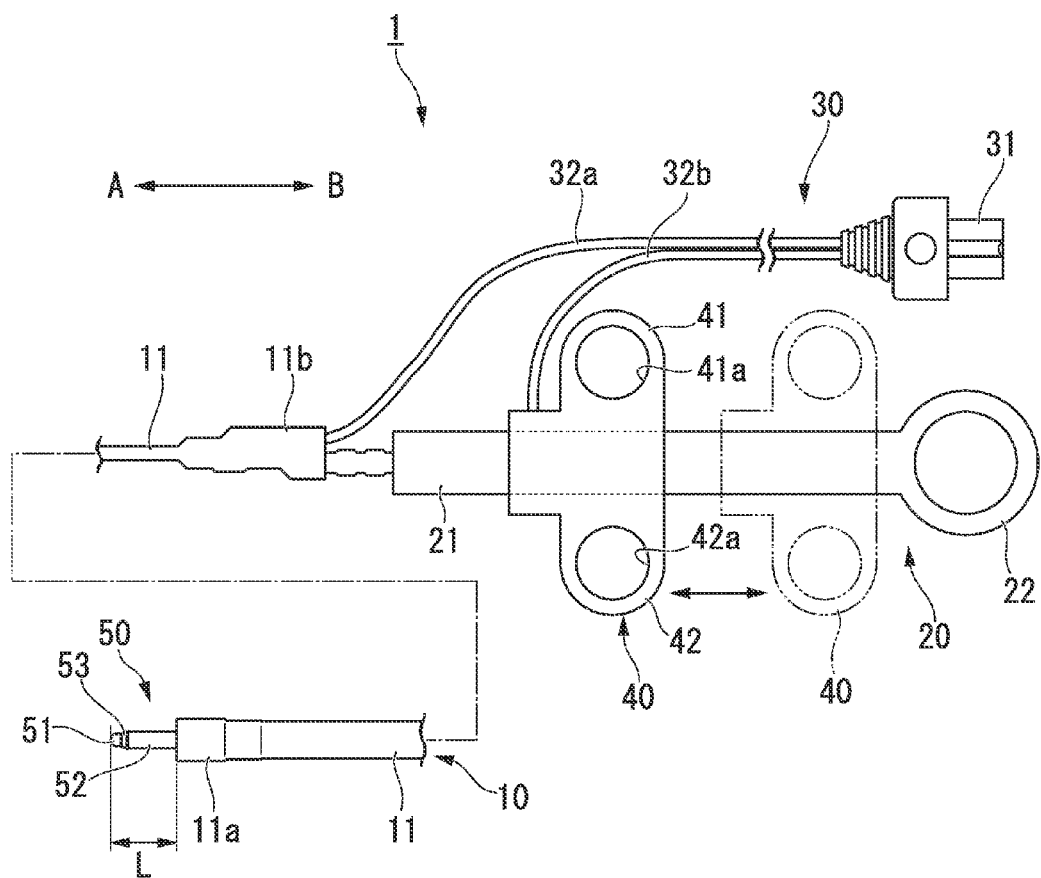
FIG. 1 is a front view showing a treatment device for electrosurgery according to a first embodiment of the present invention.

Hereinbelow, the treatment device for electrosurgery according to the first embodiment of the present invention will be described with reference to FIGS. 1 to 6. FIG. 1 is a front view showing a treatment device for electrosurgery 1 (hereinbelow, referred to as a "treatment device 1") of the present embodiment. In this drawing, the portion indicated by a reference sign 20 and the portion indicated by a reference sign 50 are shown in different scales. In addition, in the present specification, the direction indicated by a reference sign A is the distal end direction, and the direction indicated by a reference sign B is the proximal end direction.

As shown in FIG. 1, the treatment device 1 includes an insertion portion 10 that can be inserted into a body cavity, an operation portion 20 that is connected to the insertion portion 10 and receives the input of a treatment operation by a user, and a power supply portion 30 that is connected to the insertion portion 10 and the operation portion 20 and can be connected to a high-frequency power supply device (not shown).

The insertion portion 10 includes a cylindrical sheath 11 that extends in the longitudinal direction of the insertion portion 10. To a distal end portion 11a in the sheath 11, a needle-like electrode portion 50 as a treatment portion that treats a site to be treated is provided.

The operation portion 20 includes a body 21 that is fixed to a proximal end 11b of the sheath 11, a ring-like finger-hooking portion 22 that is provided to the proximal end of the body 21, and a handle 40 that is connected to the body 21 and moves forward and backward in the longitudinal direction of the body 21. The handle 40 includes finger-hooking portions 41 and 42 in which ring-like through-holes 41a and 42a for hooking fingers of a user are formed.

The power supply portion 30 includes a connector 31 that is connected to a power supply device (not shown), a power line 32a extend toward the connector 31 from the sheath 11, and a power line 32b extend toward the connector 31 from the handle 40.

Figure 2A:
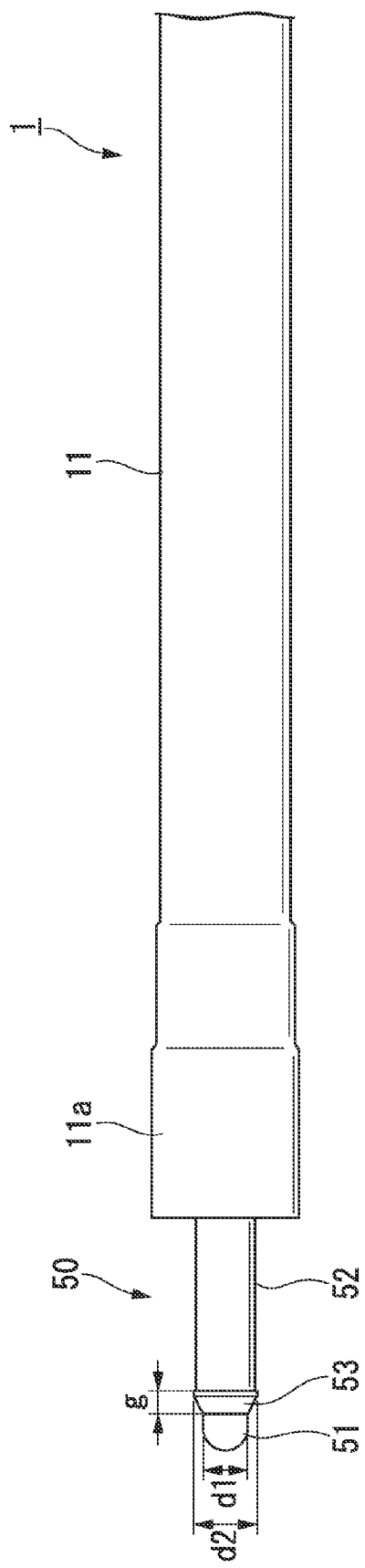
FIG. 2A is an enlarged front view showing the configuration of a portion of the treatment device for electrosurgery.

FIG. 2A is an enlarged front view showing the configuration of a portion of the treatment device 1, which shows the configuration of the distal end portion 11a of the sheath 11.

As shown in FIG. 2A, the needle-like electrode portion 50 includes, as portions that can be exposed to the outside, a first electrode 51 that is positioned at the distal end, a second electrode 52 that is positioned at the proximal end with respect to the first electrode 51, and an insulator 53 that is positioned between the first electrode 51 and the second electrode 52. In the needle-like electrode portion 50, the side of the first electrode 51 is a distal end side.

The first electrode 51 and the second electrode 52 are configured so as to contact a body tissue at the same time. Specifically, the first electrode 51 is configured with a diameter smaller than that of the second electrode 52, and the insulator 53 is formed at a slope that connects a level difference between the first electrode 51 and the second electrode 52 in the radial direction.

For example, a diameter d1 of the first electrode 51 is preferably 0.5 mm or less, and a diameter d2 of the second electrode 52 is preferably from 0.5 mm to 1.0 mm. In addition, a gap g, which is a distance between the first electrode 51 and the second electrode 52 in the axial direction toward the proximal end from the distal end of the needle-like electrode portion 50, is preferably from 0.1 mm to 0.5 mm.

The first electrode 51 is a member for incising a body tissue by contacting the body tissue, and the second electrode 52 is a passive electrode with respect to the first electrode 51. The surface area of the second electrode 52 is larger than that of the first electrode 51. Moreover, in a state where both the first electrode 51 and the second electrode 52 contact the body tissue, the contact area between the first electrode 51 and the body tissue is preferably smaller than the contact area between the second electrode 52 and the body tissue.

Figure 2B:
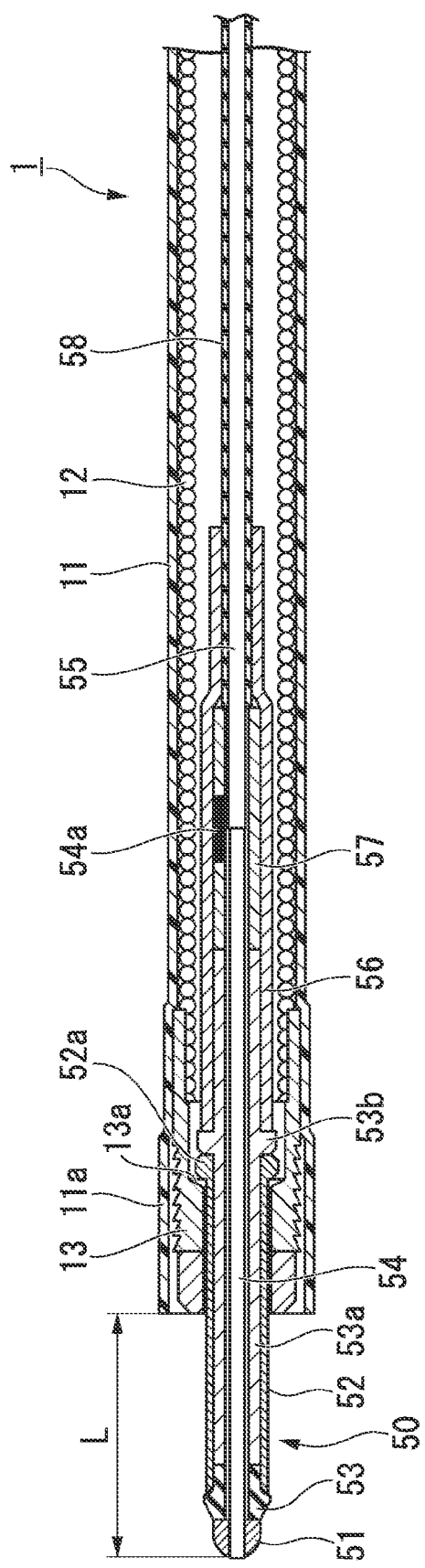
FIG. 2B is an enlarged cross-sectional view showing the configuration of a portion of the treatment device for electrosurgery.

FIG. 2B is an enlarged cross-sectional view showing the configuration of a portion of the treatment device 1.

As shown in FIG. 2B, a conductive wire 54 that extends in the proximal end direction is fixed to the first electrode 51. A conductive wire 55 is also fixed to a proximal end portion 54a of the wire 54 and further extends to the proximal end. In addition, in the circumferential surface of the wire 55, an insulation portion 58 having an insulation property is formed.

The second electrode 52 is formed in cylindrical shape, and is inserted into a conductive contact member 13 that is fixed to the distal end portion 11a of the sheath 11, so as to freely move forward and backward. In the proximal end portion of the second electrode 52, a flange portion 52a is formed in a shape of a flange protruding to the outside in the radial direction. In the contact member 13, a step portion 13a is formed to have a contact surface concentric to the flange portion 52a. When the flange portion 52a contacts the step portion 13a, the second electrode 52 becomes conductive with the contact member 13. In addition, when the step portion 13a contacts the flange portion 52a, relative movement between the sheath 11 and the needle-like electrode portion 50 is restricted such that the distal end of the first electrode 51 protrudes from the distal end of the sheath 11 by a length L.

The wire 54 is inserted into the second electrode 52. The wire 54 and the second electrode 52 are concentrically supported by being fixed to each other due to a second insulator 53a interposed between the second electrode 52 and the wire 54. The second insulator 53a includes a flange portion 53b that is adjacent to the proximal end of the flange portion 52a of the second electrode 52. In addition, cylindrical members 56 and 57 having an insulation property are fixed to the more proximal end of a flange portion 53b in the second insulator 53a.

In the distal end portion 11a of the sheath 11, the contact member 13 is fixed and electrically connected to a conductive coil sheath 12. The coil sheath 12 of the present embodiment is a multi-thread coil that is formed while being densely wound in a spiral in the circumferential direction of the sheath 11 along the inner wall of the sheath 11.

The coil sheath 12 is also a driving force-transmitting member that transmits a driving force of forward and backward operations in the axial direction or a rotation operation around the axis of the sheath 11, which is caused when the user operates the treatment device 1, to the distal end portion 11a from the proximal end portion 11b.

Figure 3:
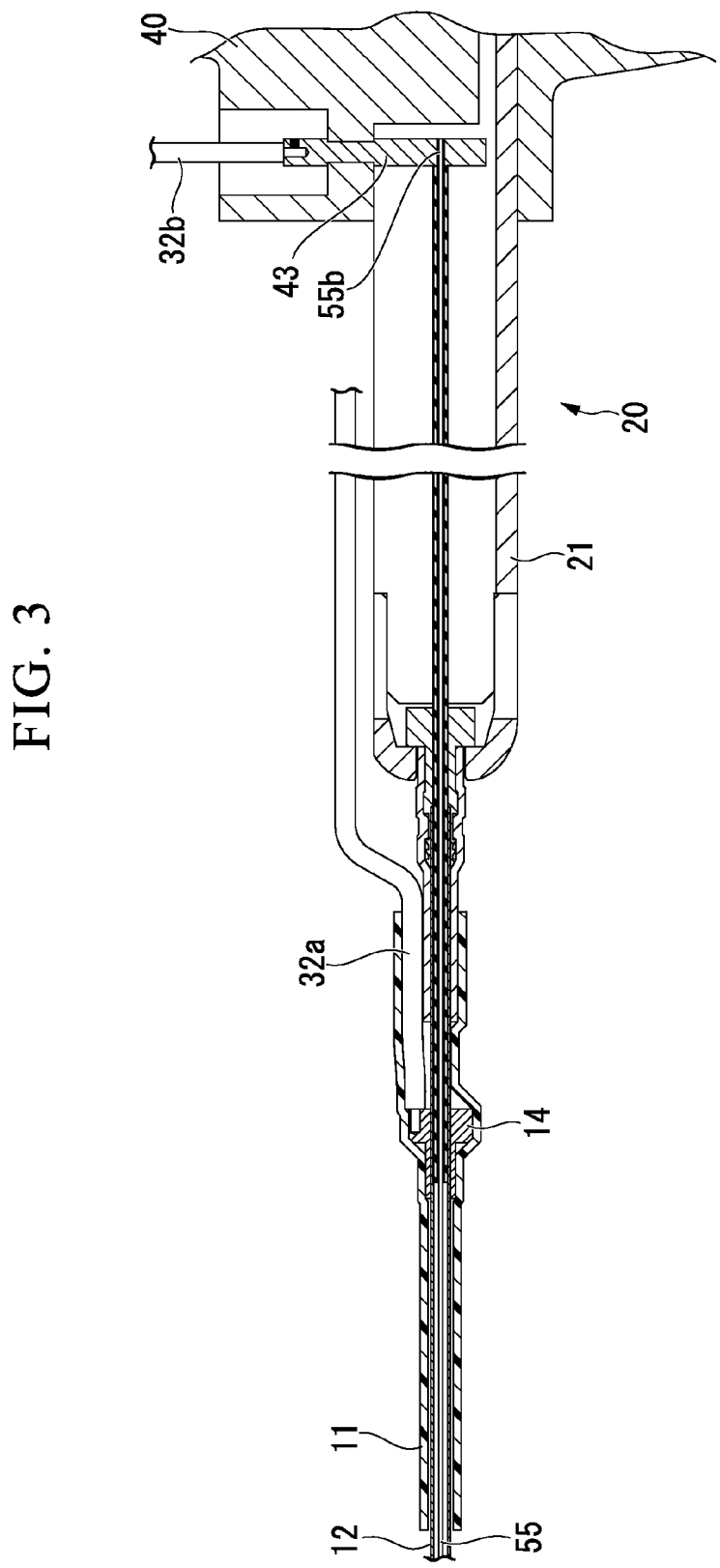
FIG. 3 is an enlarged cross-sectional view showing the configuration of a portion of the treatment device for electrosurgery.

FIG. 3 is an enlarged cross-sectional view showing the configuration of a portion of the treatment device 1.

As shown in FIG. 3, the sheath 11 is fixed to the distal end of the operation portion 20. The coil sheath 12 and the wire 55 inserted into the sheath 11 extend to the operation portion 20.

The coil sheath 12 is fixed and electrically connected to a contact member 14 positioned inside the sheath 11 at the distal end of the operation portion 20. In addition, the contact member 14 is electrically and physically connected to the power line 32a. In the contact member 14, a through-hole in which the wire 55 can be inserted while freely moving forward and backward is formed.

The wire 55 further extends toward the operation portion 20 through the through-hole of the contact member 14, and is disposed inside the body 21 of the operation portion 20. A proximal end 55b of the wire 55 is fixed to the power line 32b via an electrode portion 43 provided to the handle 40.

In this manner, the members from the power line 32b to the first electrode 51 are electrically connected to each other, and function as a first conductive portion to be applied with a high-frequency current.

Moreover, the members from the power line 32a, the coil sheath 12, the contact member 13, and the second electrode 52 are configured so as to be able to be electrically connected to each other, and function as a second conductive portion to be applied with a high-frequency current.

The operation at the time of using the treatment device 1 of the present embodiment that is configured as described above will be described with reference to FIGS. 4 to 5C.

Figure 4:
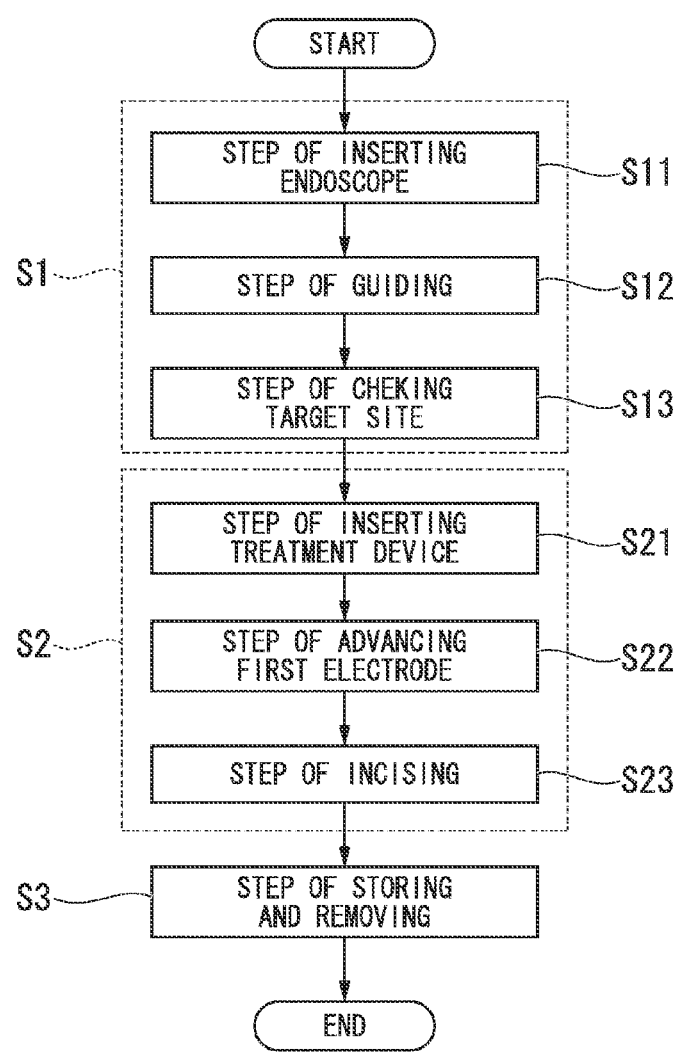
FIG. 4 is a flowchart showing the operation of the treatment device for electrosurgery.
Figure 5A:
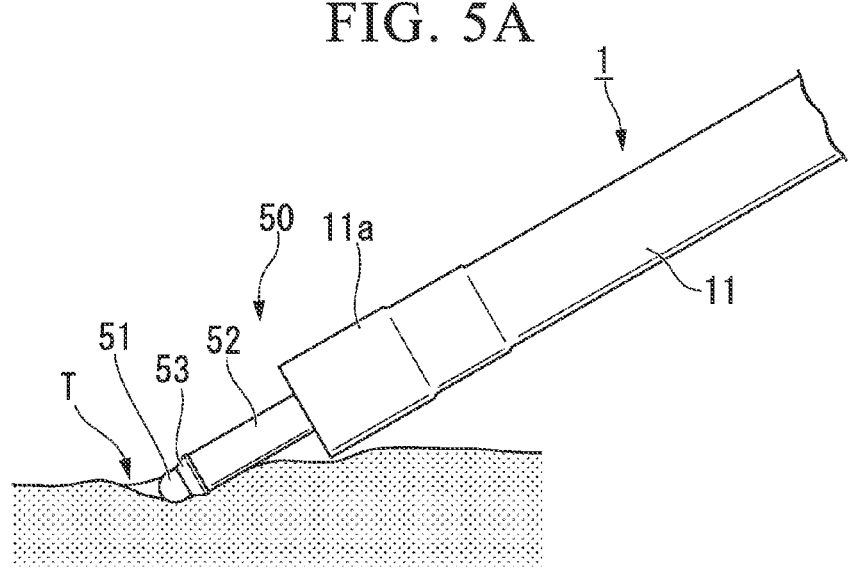
FIG. 5A is a view showing a process performed when the treatment device for electrosurgery is used.
Figure 5B:
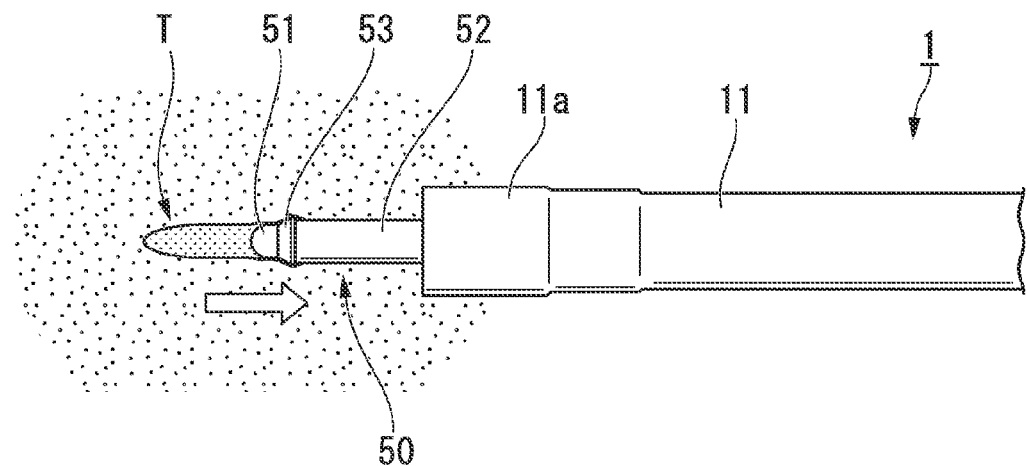
FIG. 5B is a view showing a process performed when the treatment device for electrosurgery is used.
Figure 5C:
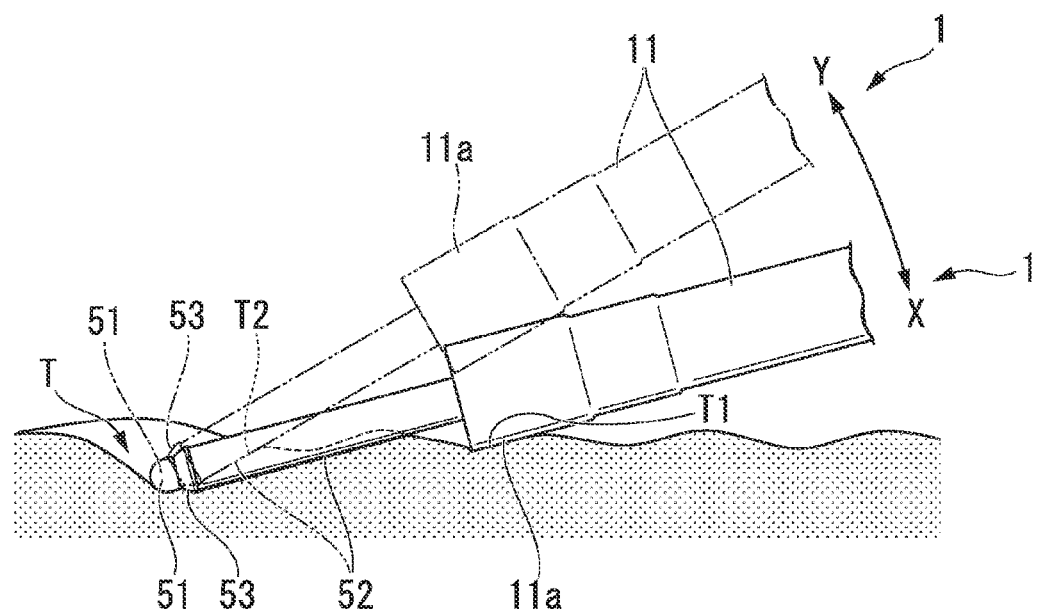
FIG. 5C is a view showing a process performed when the treatment device for electrosurgery is used.

FIG. 4 is a flowchart showing the operation of the treatment device 1, and FIGS. 5A to 5C are views showing a process performed when the treatment device 1 is used.

Step S1 is a pre-treatment step for using the treatment device 1 of the present embodiment. That is, Step S1 is a step of making it possible to endoscopically guide the treatment device 1 to a target site to be treated.

In Step S1, first, Step S11 as a step of inserting an endoscope into a body cavity is performed. In Step S11, an endoscope including an insertion portion that can be inserted into a body cavity and a treatment tool channel in which a treatment tool or the like can be inserted is inserted into a body cavity by means of an appropriate procedure according to the type or site of the target site. In order to insert the endoscope into a body cavity, the endoscope is inserted through natural orifices such as the mouth, or a small incision is made at an appropriate site so as to guide the endoscope to the target site, for example. When the endoscope is inserted into the body cavity, the process proceeds to Step S12 from Step S11.

Step S12 is a step of guiding the insertion portion of the endoscope to the target site in the body cavity.

In Step S12, the inside of the body cavity is observed using an observation optical system in the endoscope. Moreover, the endoscope is inserted into the body cavity until the distal end of the endoscope is positioned at the target site, and the distal end of the endoscope is guided to the target site.

After Step 12, Step 13 as a step of checking the target site is performed.

In Step 13, the target site is observed using the observation optical system described above, whereby the user or the like diagnoses or checks the target site.

Step S1 is completed in the above manner, and the process proceeds to Step S2.

Step S2 is a step of treating the target site by using the treatment device 1 of the present embodiment. In addition, at least before Step S2 begins, the treatment device 1 is ready in a state where the connector 31 of the power supply portion 30 is connected to a power supply device.

In Step S2, first, Step S21 begins. In Step S21, the handle 40 shown in FIG. 1 is pulled to the proximal end so as to be close to the finger-hooking portion 22. Then the wire 55 shown in FIG. 2B is pulled to the proximal end, and the needle-like electrode portion 50 is housed inside the sheath 11. In addition, in a channel for forceps of the endoscope, the sheath 11 of the treatment device 1 is inserted from the distal end portion 11a, and the distal end portion 11a is advanced from the distal end of the insertion portion. Step S21 is completed in this manner, and the process proceeds to Step S22.

Step S22 is a step of advancing the first electrode 51 of the needle-like electrode portion 50 such that the first electrode 51 can contact the target site.

In Step 22, the handle 40 shown in FIG. 1 is pushed out to the distal end of the body 21, and the needle-like electrode portion 50 is advanced from the distal end portion 11a of the sheath 11. Then the first electrode 51 stops at a point in time when the distal end thereof is advanced from the distal end portion 11a of the sheath 11 by the length L described above. At this time, as shown in FIG. 2B, the flange portion 52a of the second electrode 52 contacts the step portion 13a of the contact member 13. In addition, due to the force pushing out the handle 40, the flange portion 52a and the step portion 13a are pressed and fixed to each other. Then the second electrode 52 conduct with the contact member 13, whereby the second electrode 52 conduct with the power line 32b, and the second conductive portion to be applied with a high-frequency current is formed. Step S22 is completed in this manner, and the process proceeds to Step S23.

Step S23 is a step of incising the target site by using the needle-like electrode portion 50.

In Step S23, the first electrode 51 and the second electrode 52 of the needle-like electrode portion 50 contact a target site T, as shown in FIG. 5A. At this time, when the target site T is, for example, a soft tissue, the outer surface of each of the first electrode 51 and the second electrode 52 tightly adheres to the target site T. In the present embodiment, the area of the portion where the first electrode 51 contacts the target site T is smaller than the area of the portion where the second electrode 52 contacts the target site T. Accordingly, in the target site T, the body tissue positioned at the first electrode 51 is incised.

In a state where a high-frequency current has been applied between the first electrode 51 and the second electrode 52, the user moves the needle-like electrode portion 50 along a predetermined incision area in the target site T by operating the endoscope and the treatment device 1, as shown in FIG. 5B, for example. Then the target site T is incised along the movement trajectory of the first electrode 51 due to the high-frequency current applied, as shown in FIG. 5B.

When the user uses the treatment device 1, the positional relationship between the sheath 11 and the target site T changes in some cases. For example, as shown in FIG. 5C, between a first position X where the distal end portion 11a of the sheath 11 contacts a site T1 near the target site T and a second position Y where the distal end portion 11a of the sheath 11 contacts the site T1 near the target site T, the positional relationship between the sheath 11 and the target site T changes.

In a device for bipolar incision that includes a general needle-like electrode, a passive electrode with respect to the needle like electrode is disposed at a position corresponding to the distal end portion 11a of the sheath 11. Accordingly, in the devices used hitherto, the high-frequency current can be applied to the body tissue placed between the needle-like electrode and the passive electrode, in the first position X. However, in the devices used hitherto, the high-frequency current cannot be applied to the body tissue placed between the needle-like electrode and the passive electrode, in the second position Y.

Conversely, in the treatment device 1 of the present embodiment, whether the positional relationship between the target site T and the treatment device 1 is established in the first position X or in the second position Y, the second electrode 52 contacts a target site T2 near the target site T. Consequently, the treatment device 1 of the present embodiment can apply the high-frequency current to the body tissue placed between the first electrode 51 and the second electrode 52, at any position between the first position X and the second position Y.

When the incision of the target site T is completed, the treatment device 1 is pulled out of the body cavity, and appropriate treatment is performed on the target site T. Alternatively, the treatment is completed by pulling the treatment device 1 and the endoscope out of the body cavity (S3).

As described so far, according to the treatment device 1 of the present embodiment, the first electrode 51 is provided to the distal end of the needle-like electrode portion 50, and the relative positional relationship with respect to the first electrode 51 is fixed. In addition, the second electrode 52 is provided to the proximal end of the first electrode 51 via the insulator 53. Accordingly, even when the positional relationship of the treatment device 1 with respect to the target site T changes, the contact between the first electrode 51 as well as the second electrode 52 and the target site T is maintained. Therefore, the flow of high-frequency current applied to the target site T is suppressed from being interrupted, and the body tissue can be easily incised.

The coil sheath 12 is electrically connected to the second electrode 52 via the contact member 13. Moreover, the high-frequency current is applied to the second electrode 52 through the coil sheath 12. Accordingly, a member that transmits a driving force to the distal end portion 11a of the sheath 11 can also be used as a member for applying the high-frequency current. Consequently, complete parts inside the sheath 11 can be reduced. Therefore, the diameter of the insertion portion 10 can be reduced.

The treatment device 1 is a bipolar device that treats a target site by inserting both the first electrode 51 and the second electrode 52 into a body cavity. Therefore, it is not necessary to separately provide a passive electrode corresponding to the first electrode 51 for incising a body tissue of the target site. As a result, the treatment device 1 is easily operated.

In addition, since the high-frequency current is applied between the first electrode 51 and the second electrode 52, the area to which the high-frequency current is applied becomes a portion of the body tissue that the first electrode 51 and the second electrode 52 contact. Accordingly, compared to the device in which a passive electrode is disposed in the sheath as in the related art, incision can be performed in an area that is further localized to the position of the first electrode.

MODIFIED EXAMPLE 1

Hereinbelow, Modified Example 1 of the treatment device 1 of the present embodiment will be described with reference to FIG. 6.

Figure 6:
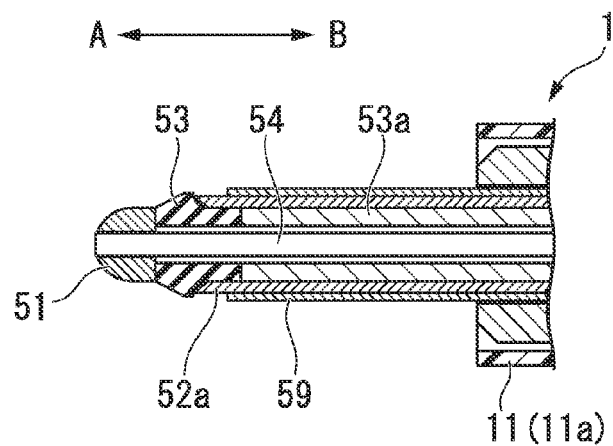
FIG. 6 is a cross-sectional view showing Modified Example 1 of the treatment device for electrosurgery.

FIG. 6 is a cross-sectional view showing the configuration of a portion of a treatment device for electrosurgery of the present modified example.

As shown in FIG. 6, in the present modified example, the treatment device 1 includes a second electrode 52a instead of the second electrode 52. In addition, a second insulator 59 having an insulation property is provided to the circumferential surface of the second electrode 52a.

The second insulator 59 is fixed to the second electrode 52a so as to cover a portion of the circumferential surface of the second electrode 52a. The second insulator 59 is disposed in the axis direction extending toward the proximal end from the distal end, while being separated from the insulator 53.

The surface area of the second electrode 52a that is exposed to the outside between the insulator 53 and the second insulator 59 is preferably the same as the surface area of the first electrode 51 that is exposed to the outside at the distal end from the insulator 53.

In the present modified example, when the first electrode 51 and the second electrode 52a contact the target site T, the area where the first electrode 51 contacts the target site T is approximately the same as the area where the second electrode 52a contacts the target site T. Accordingly, when the high-frequency current is applied to the body tissue placed between the first electrode 51 and the second electrode 52a, the body tissue in an area between the first electrode 51 and the second electrode 52a is incised in the target site T.

In the present modified example, even if the relative positional relationship between the treatment device 1 and the target site T changes, the first electrode 51 and the second electrode 52a keep contacting the body tissue. Accordingly, the flow of high-frequency current applied to the target site T is suppressed from being interrupted, and the body tissue can be easily incised.

MODIFIED EXAMPLE 2

Hereinbelow, Modified Example 2 of the treatment device 1 of the present embodiment will be described with reference to FIGS. 7A to 8D.

In the present modified example, other configuration examples of the treatment portion in the treatment device 1 will be described.

Figure 7A:
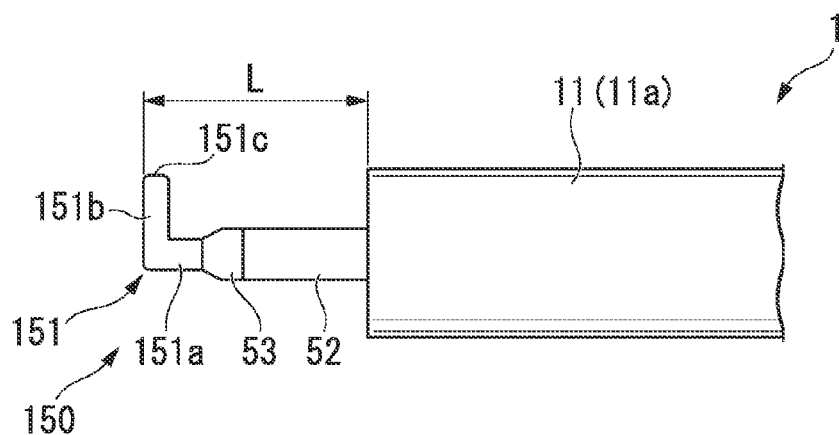
FIG. 7A is a view showing Configuration Example 1 of Modified Example 2 of the treatment device for electrosurgery.
Figure 7B:
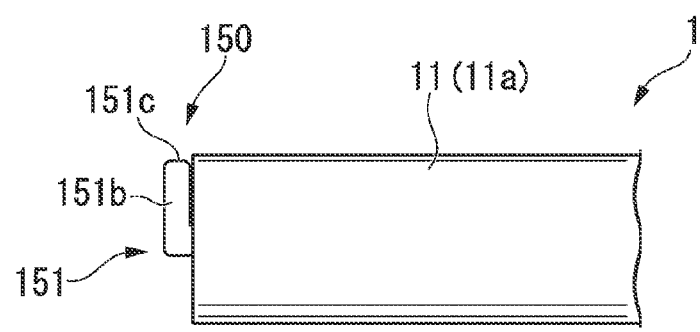
FIG. 7B is a view showing Configuration Example 1 of Modified Example 2 of the treatment device for electrosurgery.

FIGS. 7A and 7B are front views showing a first configuration example of the treatment portion in the treatment device 1 of the present modified example.

As shown in FIGS. 7A and 7B, the treatment portion in the present configuration example is a bent electrode portion 150 that is provided instead of the needle-like electrode portion 50.

The bent electrode portion 150 includes a hook-type electrode 151 instead of the first electrode 51 described above. The hook-type electrode 151 is the same as the first electrode 51 in respect that the hook-type electrode 151 is a first electrode with respect to the second electrode 52.

The hook-type electrode 151 forms a hook shape with a shaft portion 151a that extends in the distal end direction from the insulator 53 and a bent portion 151b that extends in one direction orthogonal to the axial direction of the sheath in the distal end.

In the hook-type electrode 151, the distance between the distal end of the sheath 11 and the distal end of the hook-type electrode 151 is restricted to the length L, similarly to the needle-like electrode portion 50 described above.

In the present configuration example, the hook-type electrode 151 and the second electrode 52 are brought into contact with the target site T, and the high-frequency current is applied between the hook-type electrode 151 and the second electrode 52, whereby the body tissue can be incised in the same manner as the needle-like electrode portion 50.

When the hook-type electrode 151 is brought into contact with the target site T in a direction in which a step portion 151c of the bent portion 151b is buried under the body tissue, the body tissue of the target site T can be incised at a position deeper than that of the first electrode 51.

Figure 8A:
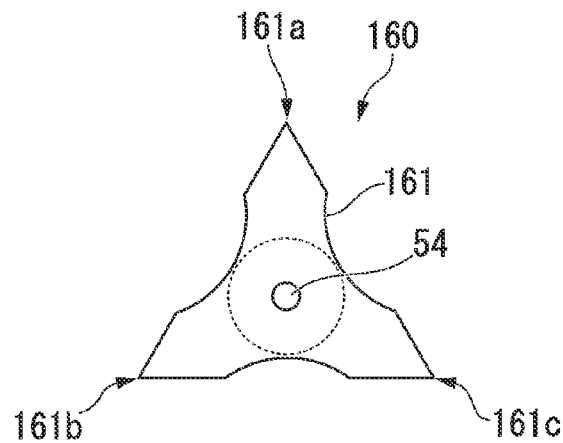
FIG. 8A is a view showing Configuration Example 2 of Modified Example 2 of the treatment device for electrosurgery.
Figure 8B:
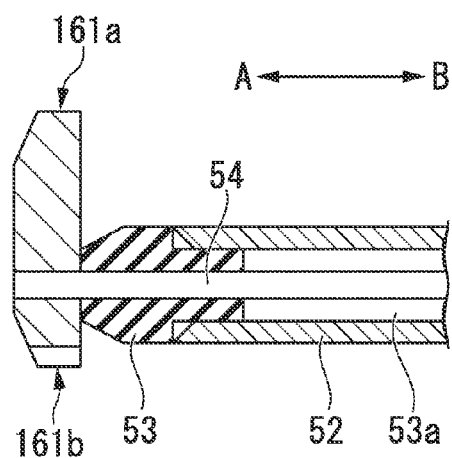
FIG. 8B is a view showing Configuration Example 2 of Modified Example 2 of the treatment device for electrosurgery.
Figure 8C:
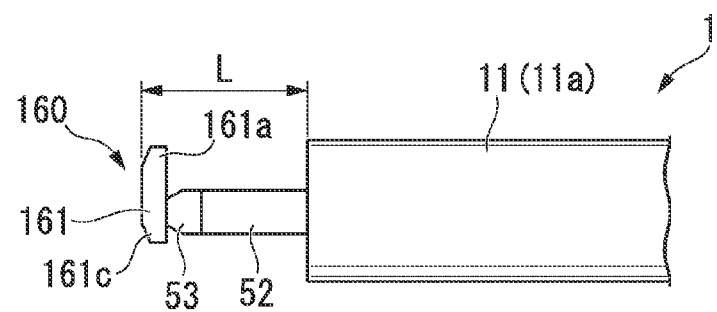
FIG. 8C is a view showing Configuration Example 2 of Modified Example 2 of the treatment device for electrosurgery.
Figure 8D:
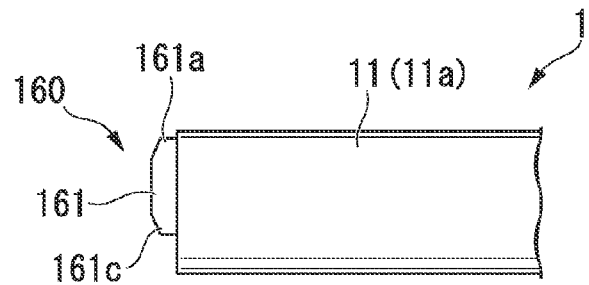
FIG. 8D is a view showing Configuration Example 2 of Modified Example 2 of the treatment device for electrosurgery.

FIGS. 8A to 8D are views showing a second configuration example of the treatment portion in Modified Example 2 of the treatment device 1. FIG. 8A is a front view, FIG. 8B is a lateral cross-sectional view, and FIGS. 8C and 8D are lateral views showing the treatment device 1 at the time of being used.

As shown FIGS. 8A and 8B, in the present configuration example, the treatment device 1 includes a triangular electrode portion 160 as a treatment portion instead of the needle-like electrode portion 50.

The triangular electrode portion 160 includes, instead of the first electrode 51, a triangular chip 161 that extends in the radial direction with respect to the axial direction extending toward the distal end from the proximal end. The triangular chip 161 is the same as the first electrode 51, in respect that the triangular chip 161 is a first electrode with respect to the second electrode 52.

In the triangular chip 161, top electrodes 161a, 161b, and 161c are formed in the positions of the vertices of an equilateral triangle having the wire 54 as a central position, which is shown in the front view of FIG. 8A.

In the present configuration example, the top electrodes 161a, 161b, and 161c can be brought into contact with the target site T such that these electrodes are hooked to the body tissue. At this time, the second electrode 52 also contacts the body tissue. Accordingly, the high-frequency current is applied between the top electrode contacting the body tissue among the top electrodes 161a, 161b, and 161c and the second electrode 52 contacting the body tissue, whereby the body tissue of the target site T can be incised. In addition, if necessary, it is possible to coagulate the target site T or the like by bringing the triangular chip 161 into contact with the body tissue such as the target site T and applying the high-frequency current between the triangular chip 161 and the second electrode 52.

MODIFIED EXAMPLE 3

Figure 9A:
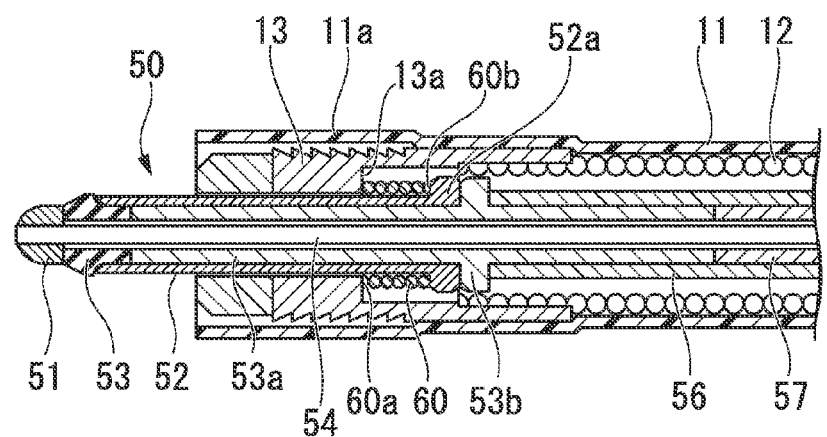
FIG. 9A is a cross-sectional view showing the configuration of Modified Example 3 of the treatment device for electrosurgery.
Figure 9B:
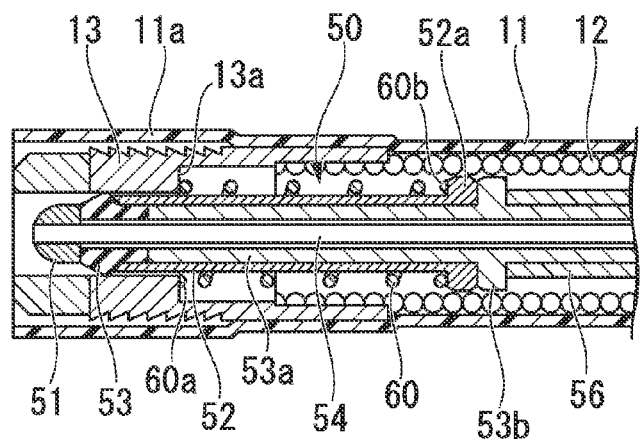
FIG. 9B is a cross-sectional view showing the configuration of Modified Example 3 of the treatment device for electrosurgery.

Hereinbelow, Modified Example 3 of the treatment device 1 of the present embodiment will be described with reference to FIGS. 9A and 9B. FIGS. 9A and 9B are cross-sectional views showing the configuration of a portion of the treatment device 1 of the present modified example.

As shown in FIGS. 9A and 9B, in the present modified example, a biasing member 60 that elongates and contracts along the axial direction of the sheath 11 is provided to the inside of the distal end portion 11a of the sheath 11. In the biasing member 60, an end portion 60a that is positioned at the distal end of the sheath 11 contacts the contact member 13.

In addition, in the biasing member 60, an end portion 60b that is positioned at the proximal end of the sheath 11 contacts the flange portion 52a.

Specifically, the biasing member 60 is configured in a shape of a coil spring of which the core material is stainless steel and the outer surface is covered with a film of gold, silver, or nickel showing higher conductivity compared to the stainless steel. In addition, the biasing member 60 has elasticity and electrical conductivity. The biasing member 60 biases the contact member 13 and the flange portion 52a in a direction in which the contact member 13 is separated from the flange portion 52a in the axial direction of the sheath 11.

The treatment device 1 of the present modified examples includes, as routes for applying the high-frequency current to the second electrode 52, a route in which the flange portion 52a at the proximal end of the second electrode 52 becomes conductive with the contact member 13 via the biasing member 60, and a route in which the circumferential surface of the second electrode 52 conduct with the contact member 13.

At this time, when the length by which the needle-like electrode portion 50 protrudes from the distal end portion 11a of the sheath 11 is shorter than the length L shown in FIG. 1, the flange portion 52a is separated from the contact member 13 in the axial direction of the sheath 11. However, since the biasing member 60 undergoes elastic deformation so as to elongate in the axial direction of the sheath 11, the high-frequency current is kept being applied between each of the contact member 13 and the flange portion 52a and the biasing member 60.

The treatment device 1 of the present modified example includes a route for applying the high-frequency current to the second electrode 52 via the biasing member 60, in addition to a route for bringing the circumferential surface of the sheath 11 into contact with the contact member 13. Accordingly, the treatment device 1 of the present modified example can reliably apply the high-frequency current to the second electrode 52, regardless of the protruding amount by which the needle-like electrode portion 50 protrudes from the sheath 11. As a result, according to the treatment device 1 of the present modified example, it is possible to use the treatment device 1 in a state where the protruding amount by which the needle-like electrode portion 50 protrudes from the distal end portion 11a of the sheath 11 has been adjusted to a protruding amount of protrusion that is optimal for treating the target site T.

(Second Embodiment)

Next, a treatment device for electrosurgery according to the second embodiment of the present invention will be described. In the respective embodiments described below, the portions common to those in the configuration of the treatment device for electrosurgery according to the first embodiment are marked with the same reference signs, and description thereof is omitted.

Figure 10:
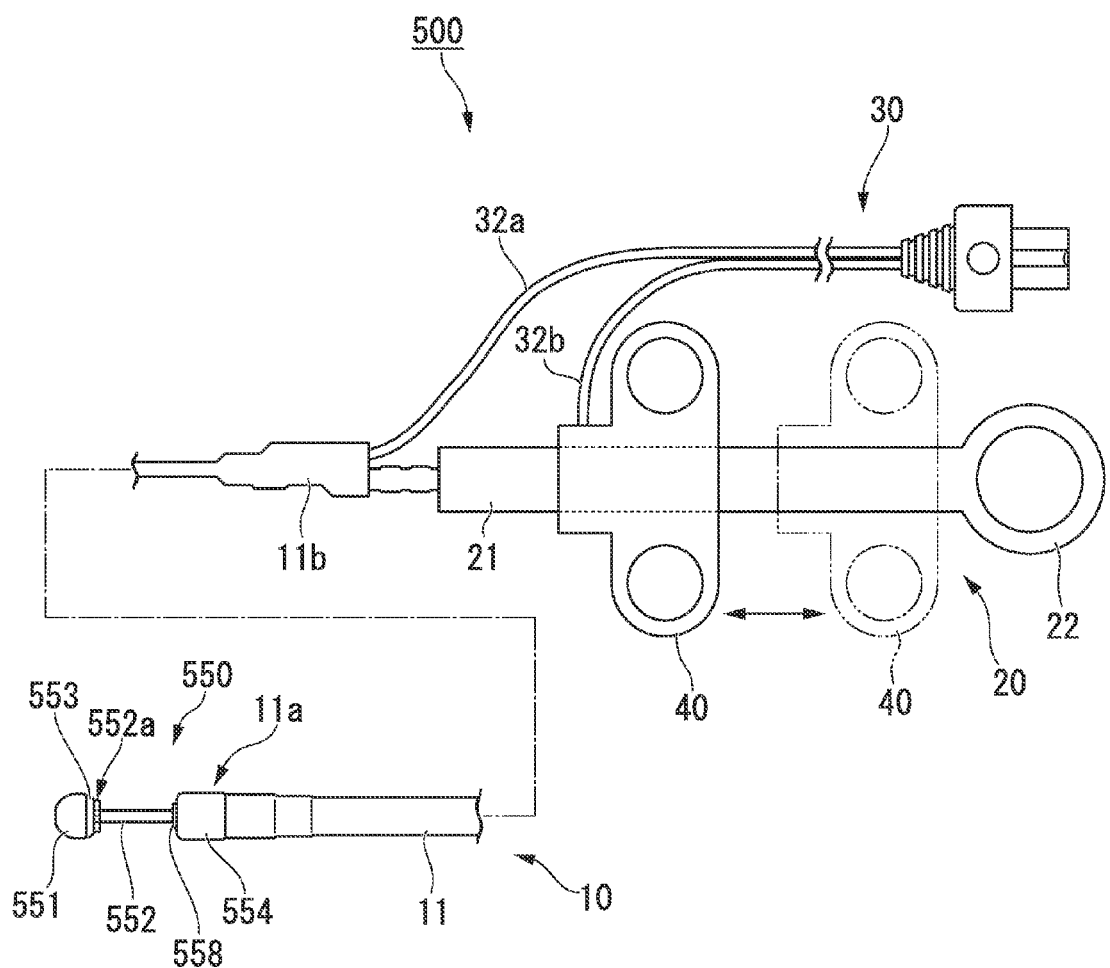
FIG. 10 is a front view showing a treatment device for electrosurgery according to a second embodiment of the present invention.
Figure 11:
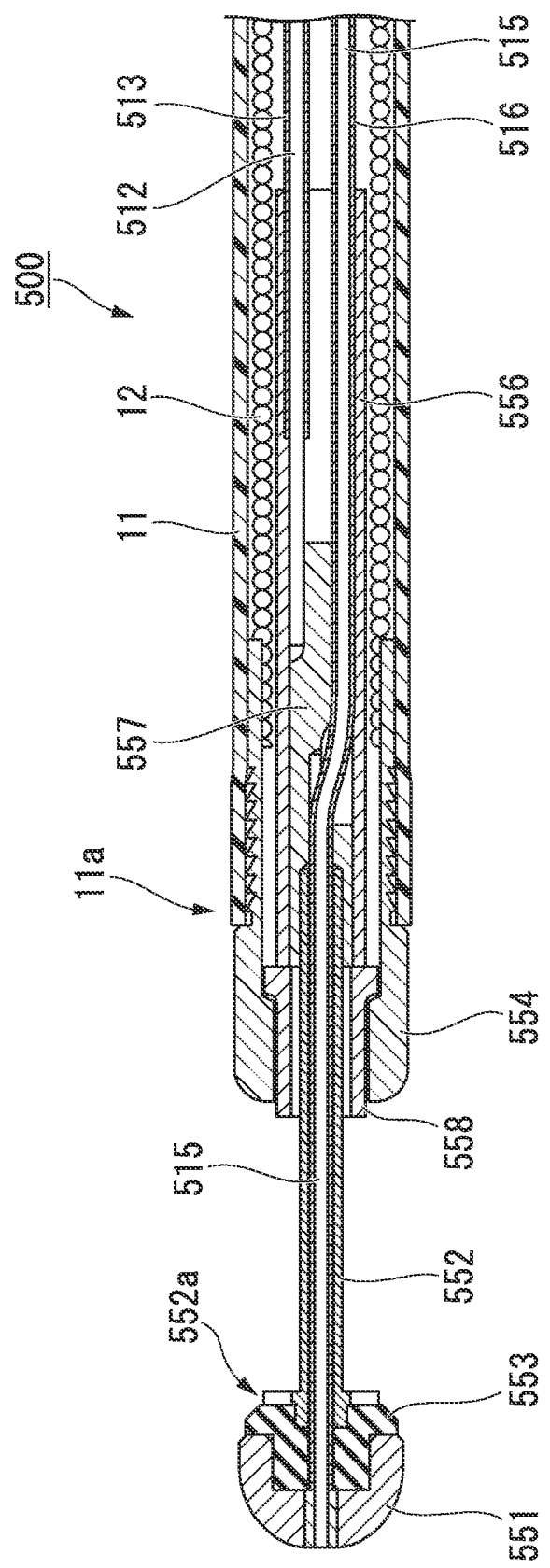
FIG. 11 is an enlarged cross-sectional view showing the configuration of a portion of the treatment device for electrosurgery.

First, the configuration of a treatment device for electrosurgery 500 (hereinbelow, referred to as a "treatment device 500") of the present embodiment will be described with reference to FIGS. 10 and 11. FIG. 10 is a front view showing the treatment device 500, and FIG. 11 is a cross-sectional view showing the configuration of a portion of the treatment device 500.

As shown in FIG. 10, the configuration of the treatment device 500 is different from the configuration of the treatment device 1 in respect that the treatment device 500 includes a needle-like electrode portion 550 provided instead of the needle-like electrode portion 50 and an enlarged passive electrode 554 provided instead of the distal end portion 11a of the sheath 11.

The needle-like electrode portion 550 includes a first electrode 551 that is positioned at the distal end, a second electrode 552 that is positioned at the proximal end with respect to the first electrode 551, and an insulator 553 that is positioned between the first electrode 551 and the second electrode 552.

The first electrode 551 is formed in a semispherical shape (including an approximately semispherical shape) that bulges to the outside in the radial direction of the second electrode 552 in the proximal end and decreases its diameter toward the distal end.

As shown in FIG. 11, the distal end of a first conductive portion 515 that extends in the axial direction of the sheath 11 is fixed to the first electrode 551 by, for example, laser welding. The first conductive portion 515 is formed of an electro-conductive wire rod. In addition, the first conductive portion 515 extends from the distal end portion 11a of the sheath 11, coaxially with the central axis of the sheath 11. Inside the sheath 11, the first conductive portion 515 is deviated due to an approximately cylindrical connecting member 557 so as to be located at a position eccentric from the central axis of the sheath 11. The first conductive portion 515 extends toward the operation portion 20 inside the sheath 11. An insulating film 516 having an insulation property is provided to the circumferential surface of the first conductive portion 515. The insulating film 516 is formed of, for example, a resin.

The second electrode 552 is formed in cylindrical shape that extends in the axial direction of the sheath 11. An extending portion 552a extending to the outside in the radial direction is integrally formed in the distal end of the second electrode 552. The extending portion 552a is formed in, for example, a shape in which three projections that extend toward the outside of the radial direction of the second electrode 552 are provided every 120° in the circumferential direction, based on the axis of the second electrode 552 as a center. The shape and number of the projections can be set to appropriate shapes and numbers.

The proximal end of the second electrode 552 is fixed to a second conductive portion 512 via the connecting member 557. The connecting member 557 has electrical conductivity, and the high-frequency current can be applied between the second conductive portion 512 and the second electrode 552.

The insulator 553 is fixed to the proximal end of the first electrode 551. In addition, as the material of the insulator 553, the same material as that of the insulator 53 of the first embodiment can be used. In the present embodiment, the insulator 553 is formed of, for example, an insulating material such as a ceramic.

In the present embodiment, unlike the treatment device 1 of the first embodiment, the first electrode 551 is a passive electrode with respect to the second electrode 552. In addition, the second electrode 552 functions as an incision electrode for incising an adult tissue. That is, in a state where both the first electrode 551 and the second electrode 552 are contacting the body tissue, the contact area between the first electrode 551 and the body tissue is set so as to be larger than the contact area between the second electrode 552 and the body tissue.

The same electric potential as that of the first electrode 551 is supplied to the enlarged passive electrode 554, and the enlarged passive electrode 554 functions as a passive electrode. As shown in FIG. 11, a portion of the enlarged passive electrode 554 is inserted into the distal end portion 11a of the sheath 11, and the material of the enlarged passive electrode 554 is, for example, stainless steel. Moreover, the enlarged passive electrode 554 has electrical conductivity.

The enlarged passive electrode 554 is connected to the coil sheath 12 inside the sheath 11. The enlarged passive electrode 554 is connected to the coil sheath 12 by means of, for example, laser welding. In addition, the high-frequency current can be applied between the enlarged passive electrode 554 and the sheath 12. In the present embodiment, the coil sheath 12 and the first conductive portion 515 function as conductive portions having the same electrical potential.

An insulator 558 having an insulation property is interposed between the enlarged passive electrode 554 and the second electrode 552.

The insulator 558 is provided while protruding toward the distal end from the enlarged passive electrode 554. Accordingly, in the positional relationship in which the insulator 558 contacts an extending portion 551a, the insulator 558 does not contact the enlarged passive electrode 554.

The operation at the time of using the treatment device 500 of the present embodiment having the configuration described above will be described with reference to FIGS. 12A to 12C.

Figure 12A:
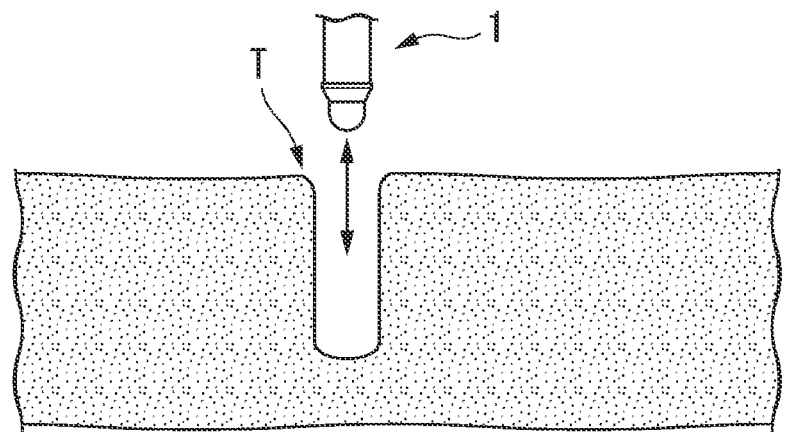
FIG. 12A is a view showing an operation performed when the treatment device for electrosurgery is used.
Figure 12B:
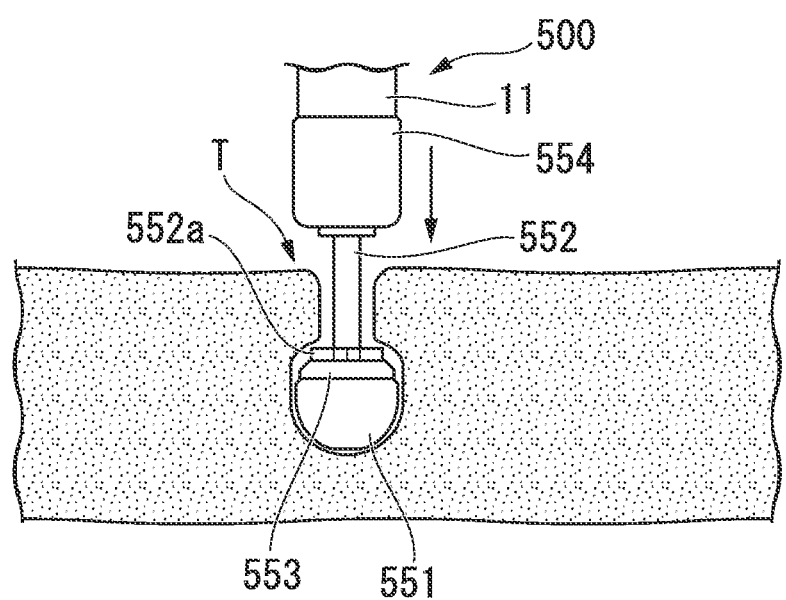
FIG. 12B is a view showing an operation performed when the treatment device for electrosurgery is used.
Figure 12C:
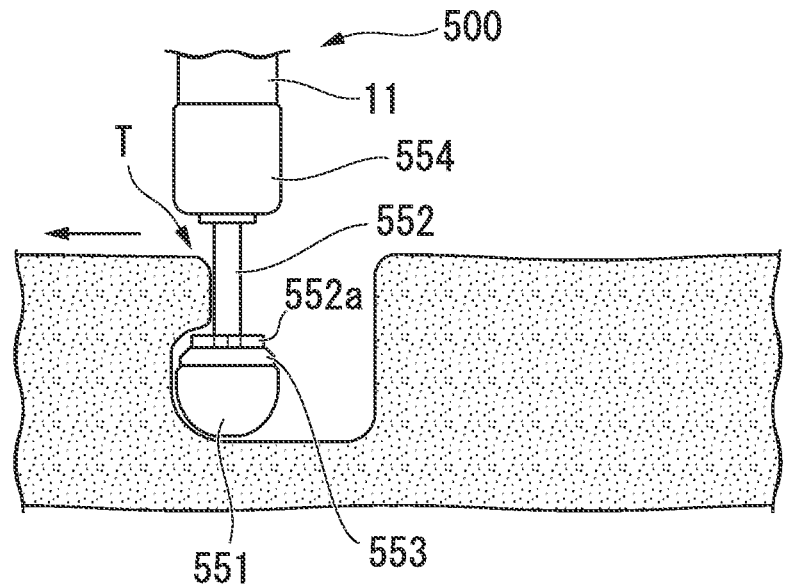
FIG. 12C is a view showing an operation performed when the treatment device for electrosurgery is used.

FIGS. 12A to 12C are views for illustrating the operation at the time of using the treatment device 500.

First, as shown in FIG. 12A, by using a known high-frequency incision device or the treatment device 1 described in the first embodiment, a small incision to be a starting point of the incision is made in the target site T.

Subsequently, as shown in FIG. 12B, the first electrode 551 of the treatment device 500 is inserted into an aperture that has been formed in the target site T due to the small incision. In the present embodiment, the user inserts the first electrode 551 straightly into the aperture formed in the target site T, in the depth direction of the aperture. Then the bottom of the aperture of the target site T contacts the outer surface of the first electrode 551, and the second electrode 552 and the extending portion 552a contact the sidewall portion of the aperture.

The user of the treatment device 500 applies the high-frequency current to the treatment device 500. In the treatment device 500, the high-frequency current is applied between the first electrode 551 and the second electrode 552 via the target site T. As a result, the target site T contacting the second electrode 552 and the extending portion 552a is incised with cauterization. While the high-frequency current is being applied to the target site T, the user moves the needle-like electrode portion 550 in the direction of incision as shown in FIG. 12C. Then the proximal end in the first electrode 551 moves in the direction of incision as the target site T is incised while being hooked on the target site T.

At this time, if necessary, the enlarged passive electrode 554 may contact the body tissue around the target site T.

As described so far, according to the treatment device 500 of the present embodiment, the first electrode 551 that functions as a passive electrode is in a positional relationship in which the first electrode 551 is buried inside the target site T. Accordingly, while the target site T is being incised, the passive electrode is not separated from the target site T.

The second electrode 552 having a fixed positional relationship in the insulator 553 is interposed between the first electrode 551 and the second electrode 552 that is positioned at the proximal end from the first electrode 551 functions as an incision electrode incising the target site T. Accordingly, while the first electrode 551 is being buried inside the target site T, the second electrode 552 contacts the target site T. Consequently, it is not necessary to perform an operation for bringing both the first electrode 551 and the second electrode 552 into contact with the target site T. As a result, the user of the treatment device 500 can concentrate on the incision operation of the target site T.

The first electrode 551 is positioned according to the depth of the small incision formed in the target site T. Therefore, since the target site T can be incised by moving the electrode in the incision direction with the depth, the depth of the needle-like electrode portion 550 inserted into the target site T can be set to a constant depth.

Figure 13:
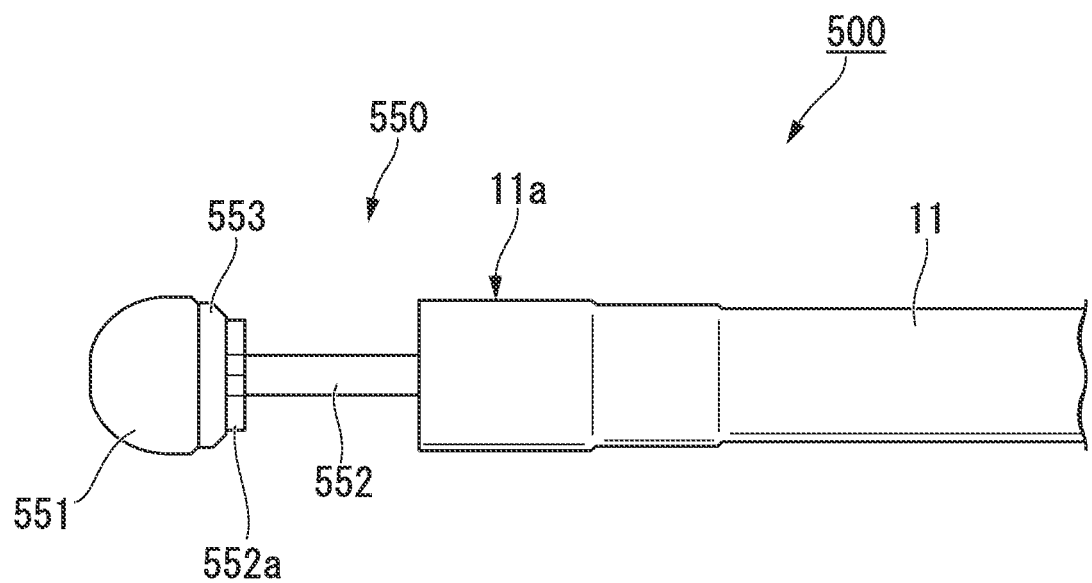
FIG. 13 is a cross-sectional view showing another configuration example of the treatment device for electrosurgery.

In addition, as shown in FIG. 13 for example, the treatment device 500 may not include the enlarged passive electrode 554. In this case, the coil sheath 12 is not necessarily a member that can be applied with the high-frequency current. Even in this case, the same effects as that of the treatment device 500 of the present embodiment can be produced.

(Third Embodiment)

Next, a treatment device for electrosurgery according to the third embodiment of the present invention will be described with reference to FIGS. 14 to 17. In the embodiments described below, the portions common to those in the configuration of the treatment device for electrosurgery according to the first embodiment are marked with the same reference signs, and description thereof is omitted.

Figure 14:
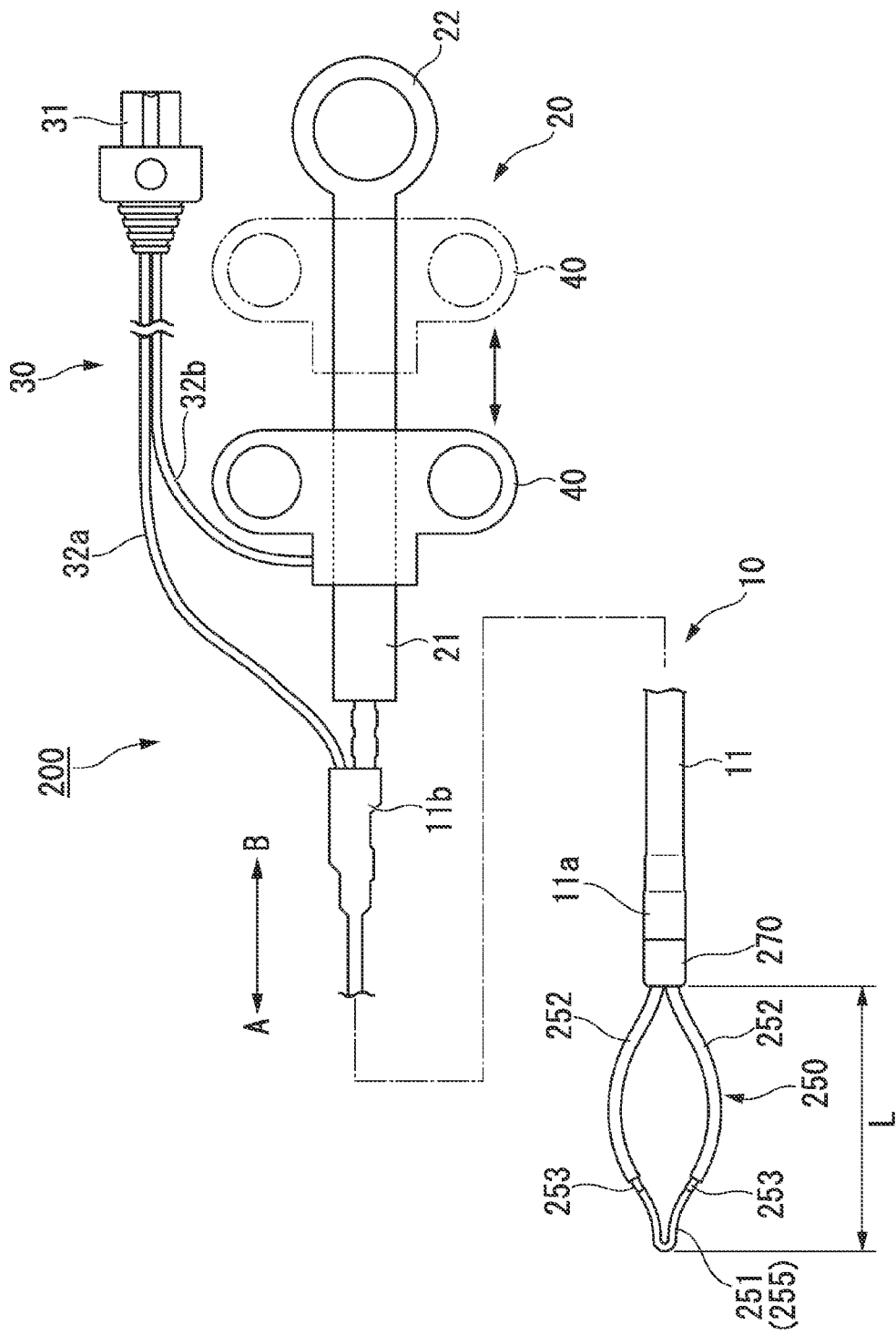
FIG. 14 is a front view showing a treatment device for electrosurgery according to a third embodiment of the present invention.

FIG. 14 is a front view showing the treatment device for electrosurgery of the present embodiment.

As shown in FIG. 14, a treatment device for electrosurgery 200 (hereinafter, referred to as a "treatment device 200") of the present embodiment includes a snare loop 250 instead of the needle-like electrode portion 50. The configuration of the treatment device 200 is different from the configuration of the treatment device 1 of the first embodiment in respect that the treatment device 200 includes a snare loop 250 instead of the needle-like electrode portion 50 and further includes an enlarged second electrode 270 provided to the outer surface of the distal end portion 11a of the sheath 11, in addition to the second electrode 52.

The snare loop 250 has a ring-like exterior. The snare loop 250 includes a conductive first electrode 251, a second electrode 252 that is positioned at the proximal end from the first electrode 251, and an insulator 253 that is positioned between the first electrode 251 and the second electrode 252.

The first electrode 251 can be applied with the high-frequency current and has elasticity. In addition, the first electrode 251 is a portion of the distal end in a wire 255 that is a core material of the snare loop 250, and is an area of the distal end from the insulator 253. The wire 255 is formed so as to make a ring-like loop by being folded back at the distal end.

The size of the first electrode 251 is set to an appropriate size according to the positional relationship between the wire 255 and the insulator 253. For example, the size of the first electrode 251 is preferably set according to the target site T, such that the outer surface of the wire 255 having a length which can be hooked around the target site T such as the neck portion of a polyp P (see FIG. 16) is exposed.

The second electrode 252 is a conductive tubular member that is provided on the circumferential surface of the wire 255 so as to cover the wire 255 via the insulator 253.

The insulator 253 is provided so as to cover the wire described above, such that at least a portion of the insulator 253 is exposed to the outside between the first electrode 251 and the second electrode 252.

Figure 15:
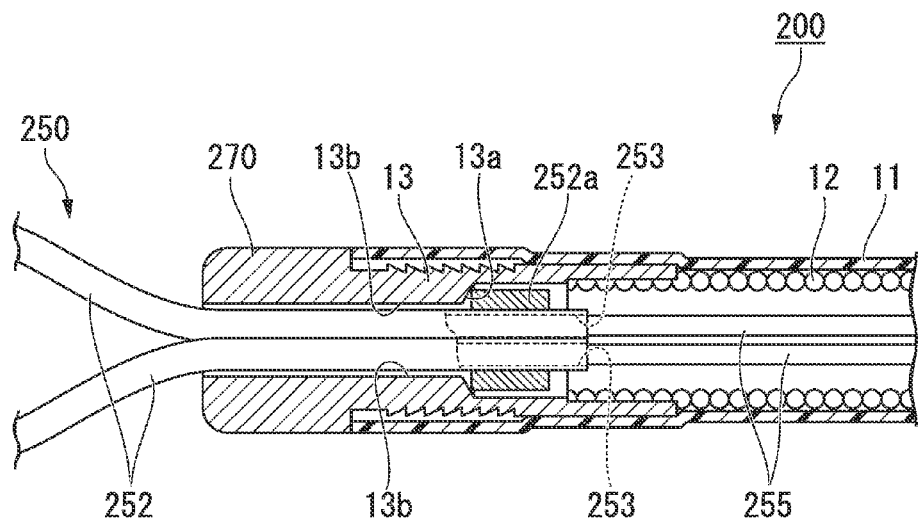
FIG. 15 is an enlarged cross-sectional view showing the configuration of a portion of the treatment device for electrosurgery.

FIG. 15 is a partial cross-sectional view showing a portion of the distal end portion 11a of the sheath 11 of the treatment device 200.

As shown in FIG. 15, the wire 255 of the snare loop 250 extends to the proximal end through the inside of the sheath 11. The end portion of the wire 255 at the proximal end is fixed to the handle 40 and the power line 32b, similarly to the treatment device 1 of the first embodiment (see FIGS. 14 and 3).

In addition, a fixing tube 252a tying two strands of the wire 255 that are formed due to the wire 255 being folded back is fixed to a portion of the proximal end in the second electrode 252. The fixing tube 252a has conductivity.

Similarly to the flange portion 52a of the first embodiment, the fixing tube 252a is a member that becomes conductive by contacting the contact member 13.

In the present embodiment, the handle 40 is caused to move to the distal end of the body 21 in the operation portion 20 shown in FIG. 14, whereby the fixing tube 252a contacts the contact member 13. Due to the contact between the fixing tube 252a and the contact member 13, the length by which the snare loop 250 protrudes from the distal end of the sheath 11 is restricted to the length L shown in FIG. 14. In addition, the electrical connection between the second electrode 252 and the contact member 13 is formed when the outer surface of the second electrode 252 contacts an inner surface 13b of the contact member 13 due to the elasticity of the wire 255.

As shown in FIGS. 14 and 15, the second electrode 252 is electrically connected to the enlarged second electrode 270, when each second electrode 252 is inserted into the enlarged second electrode 270. Moreover, the enlarged second electrode 270 is integrally molded with the contact member 13. That is, the enlarged second electrode 270 is fixed and electrically connected to the coil sheath 12 similarly to the contact member 13 while functioning as the contact member 13.

In the treatment device 200, the second electrode 252 is conductive with the enlarged second electrode 270. Accordingly, both the second electrode 252 and the enlarged second electrode 270 function as a passive electrode with respect to the first electrode 251.

Hereinbelow, the operation at the time of using the treatment device 200 will be described focusing mainly on the portions different from those in the treatment device 1.

When the treatment device 200 is used, Step S1 and Step S21 shown in FIG. 3 are performed, similarly to the treatment device 1. In Step S22 performed after Step S21, as shown in FIG. 14, the user moves the handle 40 to the distal end of the body 21, whereby the snare loop 250 is advanced from the distal end portion 11a of the sheath 11. Then, the snare loop 250 is enlarged due to the elasticity of the wire 255 and becomes a ring shape.

Figure 16:
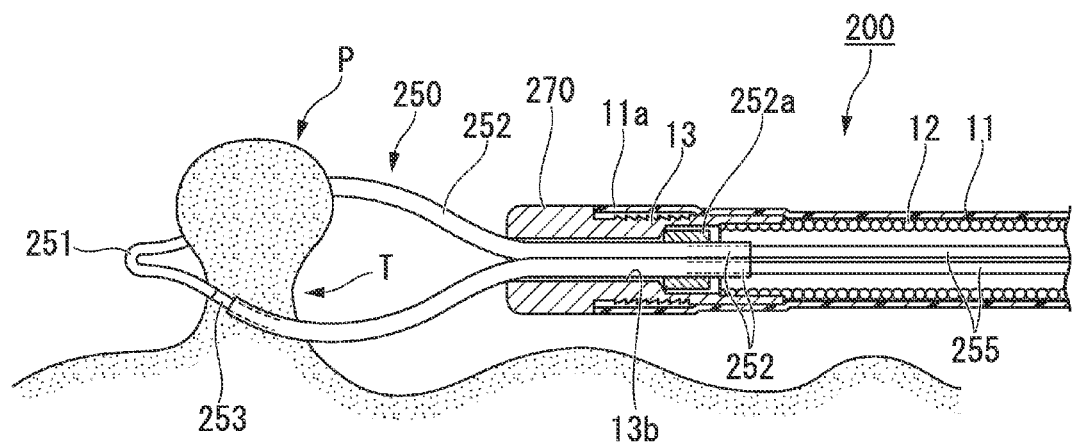
FIG. 16 is a view showing an operation performed when the treatment device for electrosurgery is used.
Figure 17:
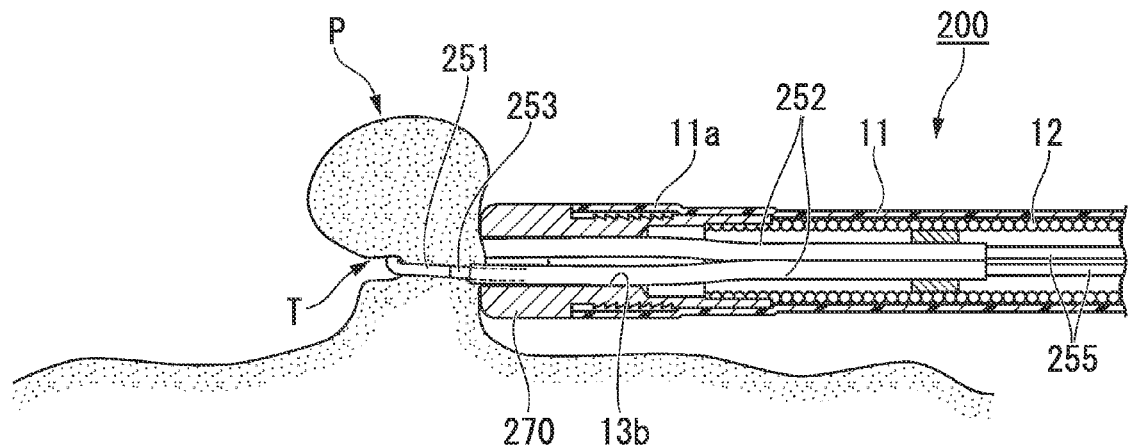
FIG. 17 is a view showing an operation performed when the treatment device for electrosurgery is used.

FIGS. 16 and 17 are views showing a process performed when the treatment device 200 is used.

In Step S23, the snare loop 250 is hooked around a neck portion of a polyp P (target site T in the present embodiment) due to the operation of the user, as shown in FIGS. 16 and 17. Subsequently, the user moves the handle 40 to the proximal end of the body 21. Then the snare loop 250 hooked around the polyp P moves to the inside of the sheath 11, and the target site T is pulled and draw by the first electrode 251 which is a portion at the distal end of the snare loop 250. At this time, the enlarged second electrode 270 is pressed on the polyp P.

Thereafter, due to the operation of the user, the high-frequency current is applied between the first electrode 251 and the second electrode 252. As a result, the target site T is incised, and the polyp P is excised.

As described so far, according to the treatment device 200 of the present embodiment, the first electrode 251 is provided to the distal end of the ring-like snare loop 250, and the second electrode 252 is provided to the proximal end of the snare loop 250 via the insulator 253. Accordingly, even if the positional relationship of the treatment device 1 is changed with respect to the target site T, the first electrode 251 and the second electrode 252 keep contacting the target site T. Consequently, the flow of high-frequency current applied to the target site T is suppressed from being interrupted, and the body tissue can be easily incised.

Figure 18A:
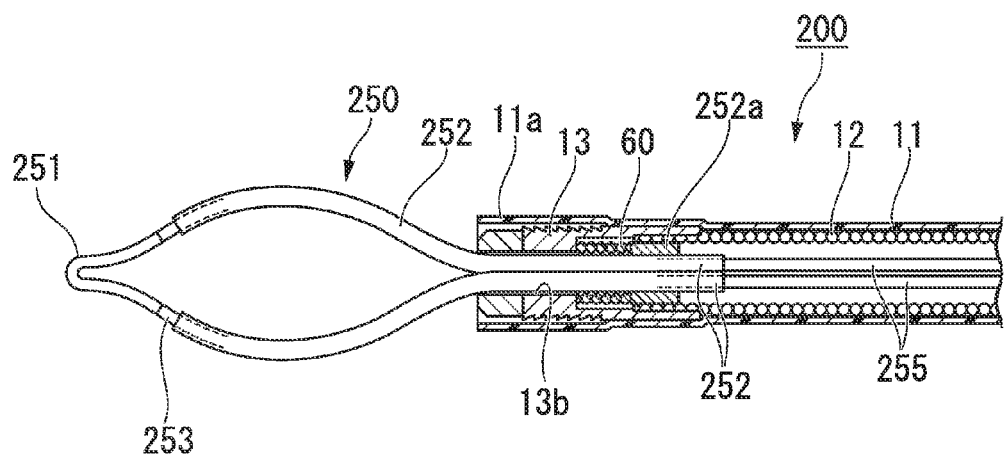
FIG. 18A is a cross-sectional view showing another configuration example of the treatment device for electrosurgery.

In the present embodiment, the biasing member 60 may be provided to the inside of the sheath 11, similarly to Modified Example 3 of the treatment device 1 of the first embodiment. Specifically, as shown in FIG. 18A, the biasing member 60 is connected to the fixing tube 252a and to the contact member 13, and biases the fixing tube 252a and the contact member 13 in the direction in which the fixing tube 252a is separated from the contact member 13 in the axial direction of the sheath 11. In this case, when the snare loop 250 is pulled to the inside of the sheath 11, it is possible to cause the contact member 13 to be reliably conductive with the second electrode 252.

Figure 18B:
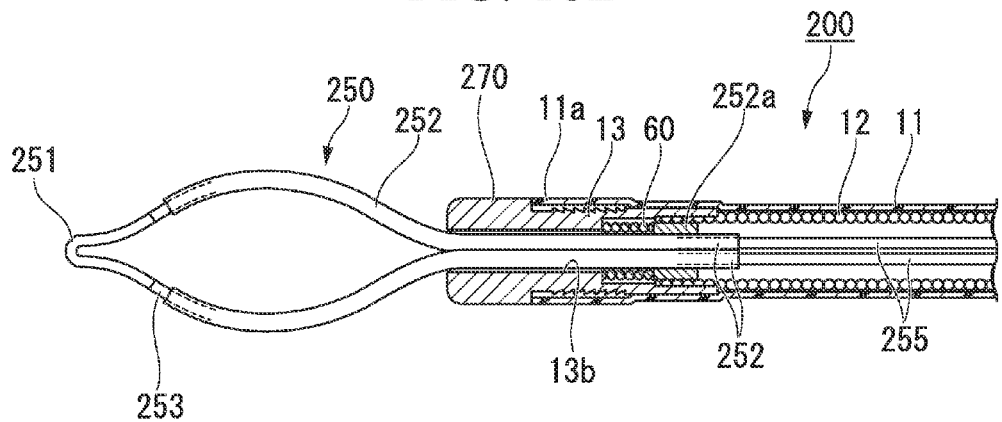
FIG. 18B is a cross-sectional view showing the other configuration example of the treatment device for electrosurgery.

In addition, as shown in FIG. 18B, the treatment device 200 may include both the biasing member 60 and the second passive electrode 270.

(Fourth Embodiment)

Next, a treatment device for electrosurgery according to the fourth embodiment of the present invention will be described with reference to FIGS. 19 to 23B.

Figure 19:
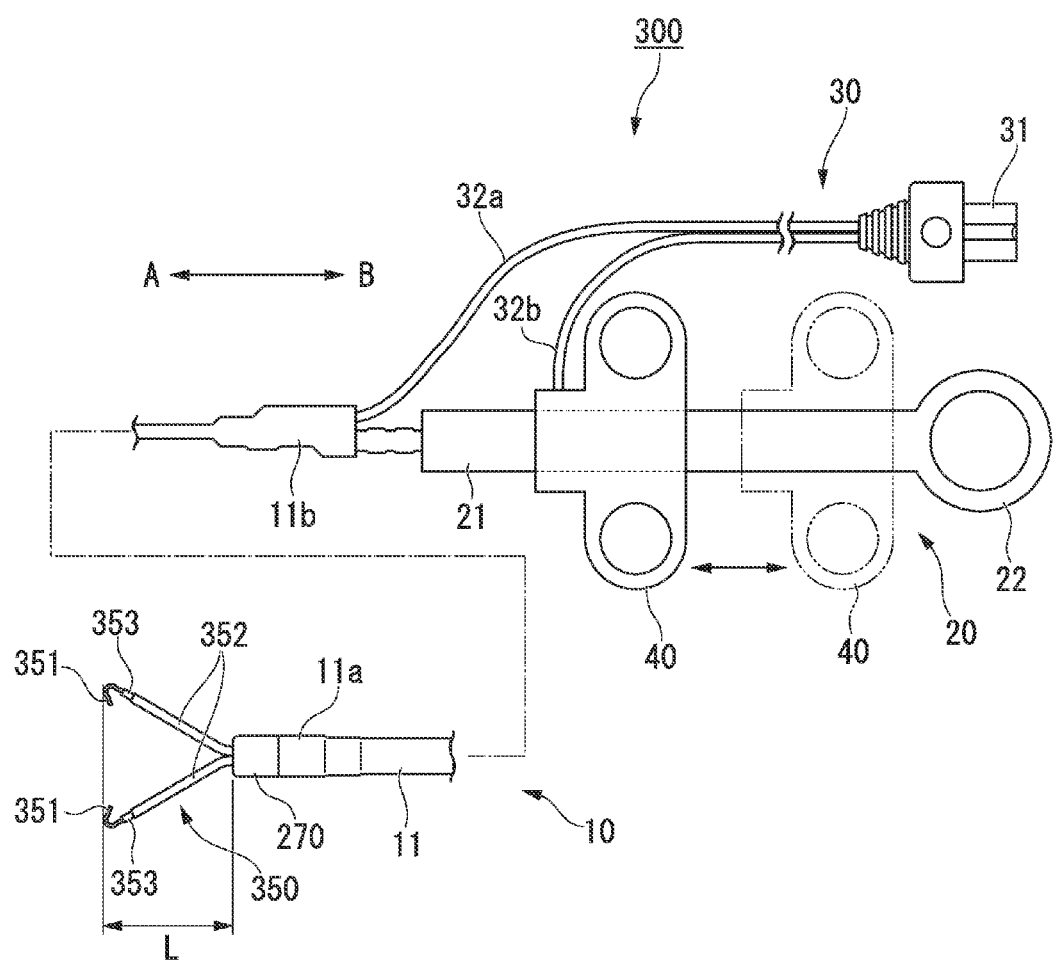
FIG. 19 is a front view showing a treatment device for electrosurgery according to a fourth embodiment of the present invention.

FIG. 19 is a front view showing the treatment device for electrosurgery of the present embodiment.

As shown in FIG. 19, a treatment device for electrosurgery 300 (hereinbelow, referred to as a "treatment device 300") of the present embodiment includes a two-legged incision portion 350 instead of the needle-like electrode portion 50.

The two-legged incision portion 350 includes a pair of elastic gripping portions 351 that is slanted so as to face the axis direction extending toward the distal end from the proximal end and to face the outer direction of the radial direction of the sheath 11.

Figure 20:
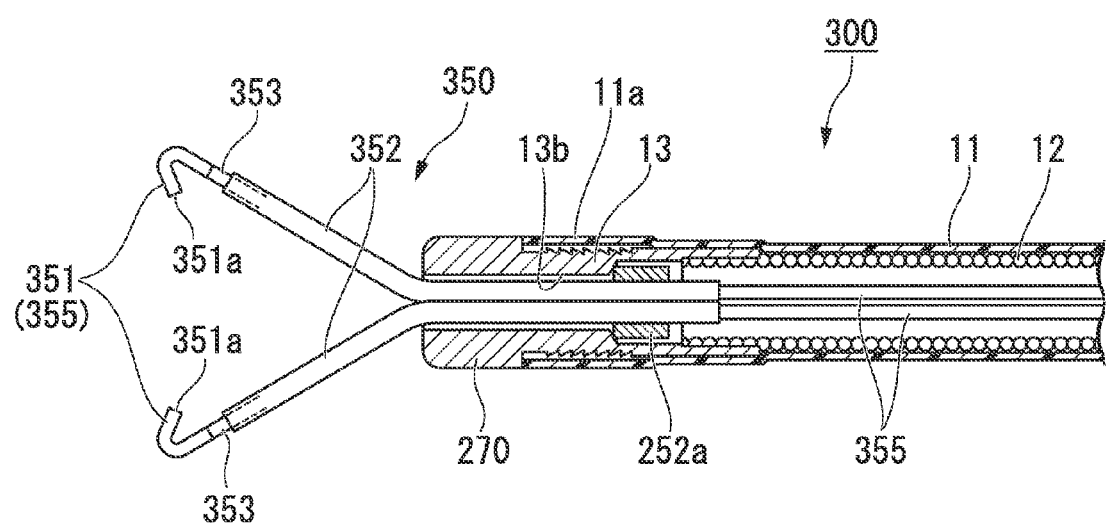
FIG. 20 is an enlarged cross-sectional view showing the configuration of a portion of the treatment device for electrosurgery.

FIG. 20 is a partial cross-sectional view showing part of the distal end portion 11a of the sheath 11 of the treatment device 300.

As shown in FIG. 20, similarly to the wire 255 shown in the second embodiment, each of the elastic gripping portions 351 includes a hooking portion 351a formed in a shape in which the end portion thereof is bent in a direction approaching the other hooking portion 351a at the distal end, in an area near the end portion of the distal end of an elastic wire 355 which can be applied with the high-frequency current.

In addition, to the proximal end of the elastic gripping portion 351, a second electrode 352 of which the relative positional relationship to the elastic gripping portion 351 is fixed and which is provided so as to cover the wire 355, and an insulator 353 which is interposed between the elastic gripping portion 351 and the second electrode 352 and fixed to cover the wire 355 are provided. In the present embodiment, the elastic gripping portion 351 is a first electrode with respect to the second electrode 352.

The proximal end portion in the second electrode 352 is fixed by being tied with a fixing cylinder 252a, similarly to the treatment device 200 of the third embodiment. In addition, the treatment device 300 includes the same enlarged second electrode 270 as that of treatment device 200.

Figure 21:
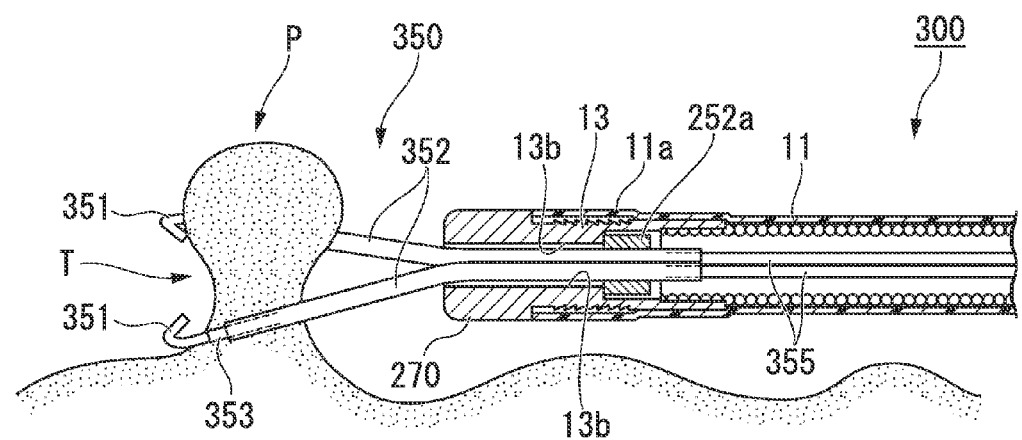
FIG. 21 is a view showing an operation performed when the treatment device for electrosurgery is used.
Figure 22:
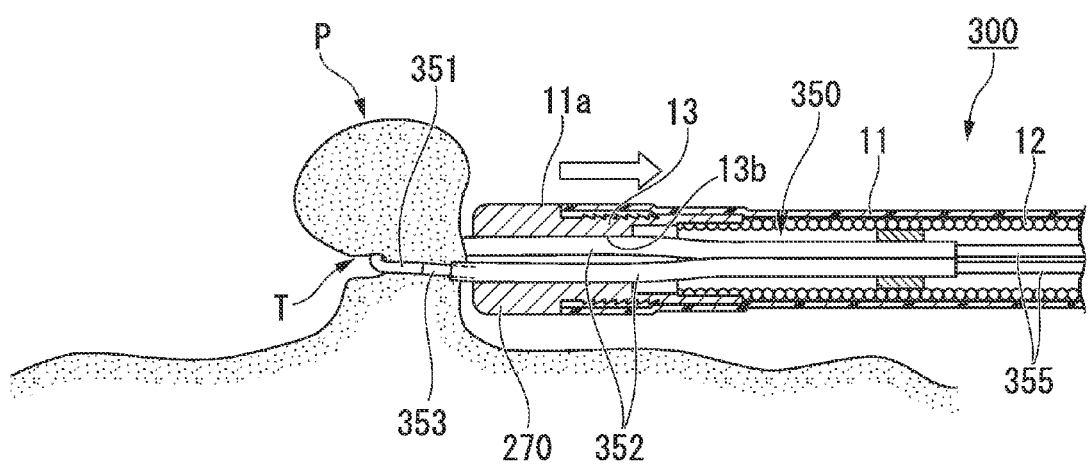
FIG. 22 is a view showing an operation performed when the treatment device for electrosurgery is used.

Hereinbelow, an example in which a neck portion of the polyp P is incised as the target site T will be described. FIGS. 21 and 22 are views showing a process performed when the treatment device 300 of the present embodiment is used.

As shown in FIG. 21, in using the treatment device 300, when the two-legged incision portion 350 has been advanced from the distal end portion 11a of the sheath 11, each of the elastic gripping portions 351 is positioned so as to be separated from each other due to the elasticity of the wire 355. In this state, by the operation of the user, the position of the two-legged incision portions 350 is adjusted such that the target site T is positioned between the pair of elastic gripping portions 351.

When the user moves the handle 40 shown in FIG. 19 to the proximal end of the body 21, the two-legged incision portion 350 moves to the inside of the sheath 11 as shown in FIG. 22, and each of the elastic gripping portions 351 operates so as to approach each other, thereby contacting the target site T. At this time, the outer surface of the second electrode 352 and the inner surface of the sheath 11, more specifically, the outer surface of the second electrode 352 and the inner surface 13*b* of the contact member 13 come in contact with each other. The second electrode 352 contacts the contact member 13 such that the second electrode 352 is pressed on the inner surface of the contact member 13 due to the elasticity of the wire 355. Accordingly, the second electrode 352 becomes conductive with the contact member 13 such that the high-frequency current can be applied therebetween. At this time, the outer surface of the polyp P contacts the enlarged second electrode 270.

Subsequently, by the operation of the user, the handle 40 further moves to the proximal end of the body 21, and the high-frequency current is applied between the elastic gripping portion 351 and the second electrode 352.

Then the body tissue positioned in the target site T is incised with cauterization between the elastic gripping portion 351 and the second electrode 352, whereby the polyp P is excised.

As described so far, according to the treatment device 300 of the present embodiment, the elastic gripping portion 351 is provided to the distal end of the two-legged incision portion 350. In addition, the second electrode 352 is provided to the proximal end of the elastic gripping portion 351 via the insulator 353. Accordingly, even if the positional relationship of the treatment device 1 is changed with respect to the target site T, the elastic gripping portion 351 and the second electrode 352 keep contacting the target site T. Consequently, the flow of high-frequency current applied to the target site T is suppressed from being interrupted, and the body tissue can be easily incised.

Figure 23A:
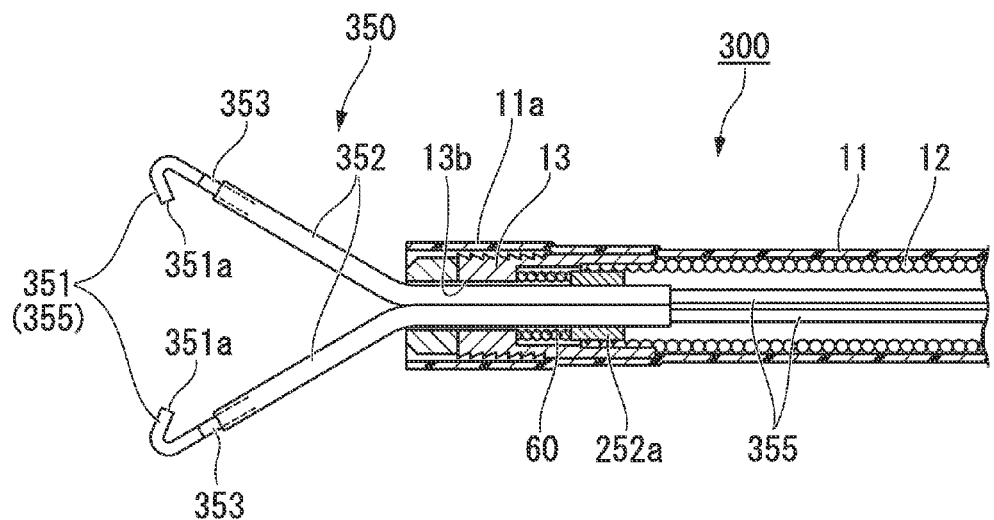
FIG. 23A is a cross-sectional view showing another configuration example of the treatment device for electrosurgery.

In the present embodiment, the biasing member 60 may be provided to the inside of the sheath 11 similarly to Modified Example 3 of the treatment device 1 of the first embodiment, as shown in FIG. 23A. In this case, when the two-legged incision portion 350 is pulled to the inside of the sheath 11, it is possible to cause the contact member 13 to be reliably conductive with the second electrode 252.

Figure 23B:
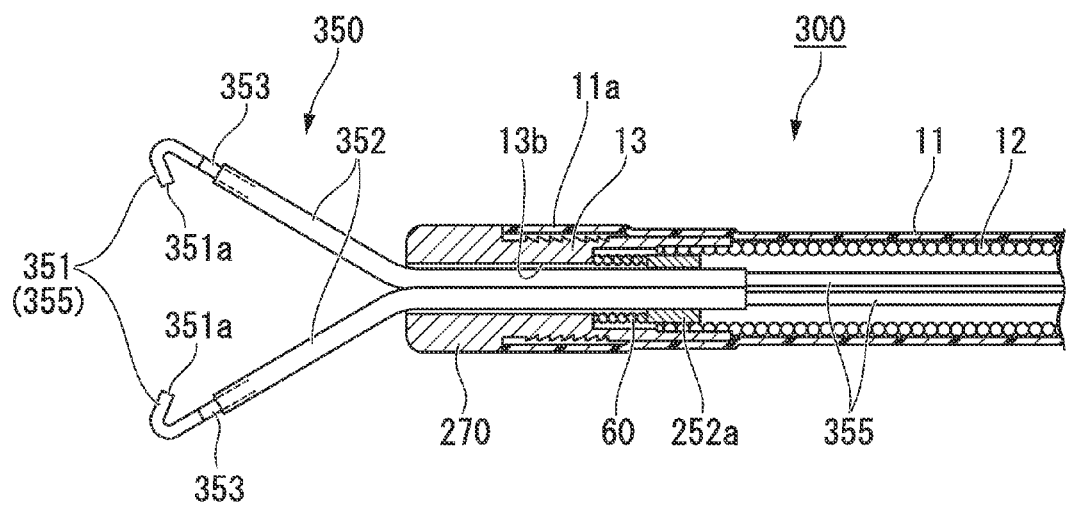
FIG. 23B is a cross-sectional view showing the other configuration example of the treatment device for electrosurgery.

In addition, as shown in FIG. 23B, the treatment device 300 may include the biasing member 60 and the second passive electrode 270.

(Fifth Embodiment)

Next, a treatment device for electrosurgery according to the fifth embodiment of the present invention will be described with reference to FIGS. 24 to 26.

Figure 24:
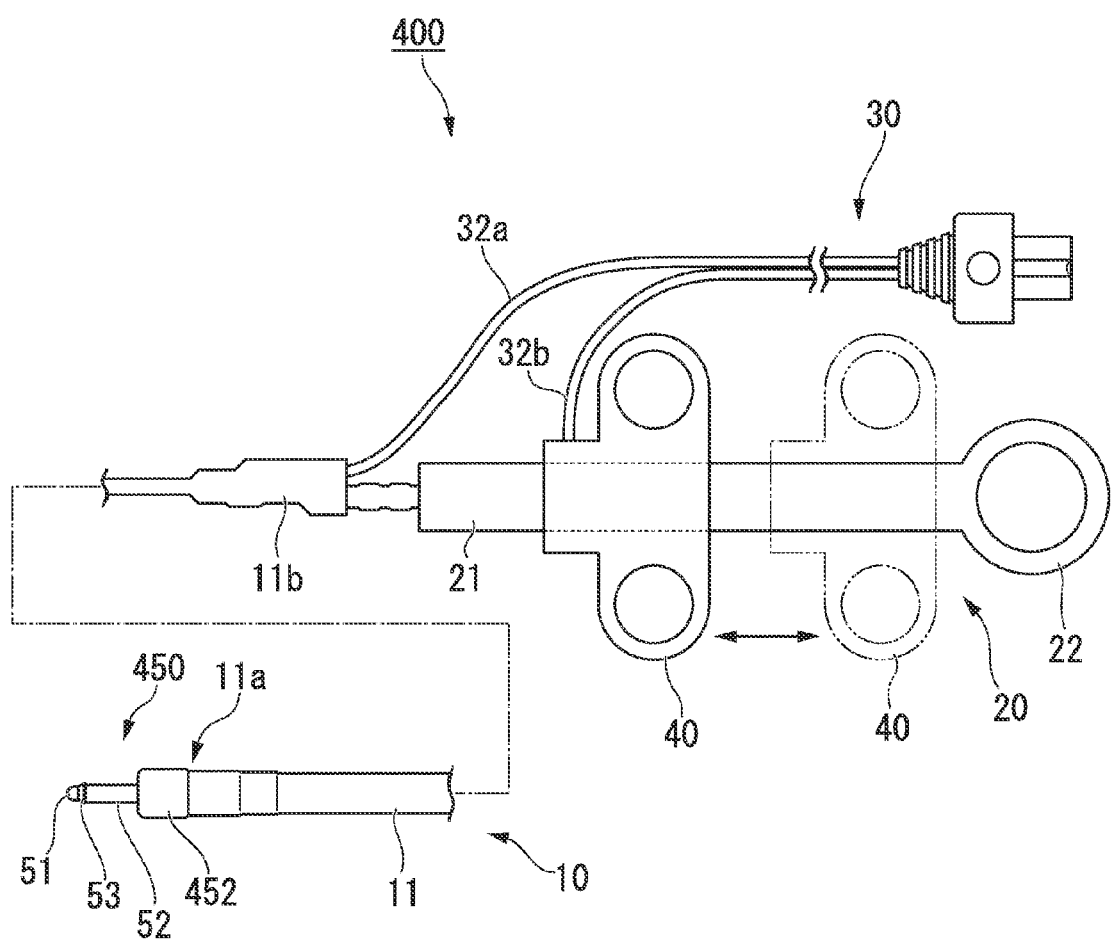
FIG. 24 is a front view showing a treatment device for electrosurgery according to a fifth embodiment of the present invention.

FIG. 24 is a front view showing the treatment device for electrosurgery of the present embodiment. As shown in FIG. 24, a treatment device for electrosurgery 400 (hereinbelow, referred to as a "treatment device 400") of the present embodiment includes a needle-like electrode portion 450 instead of the needle-like electrode portion 50. The configuration of the treatment device 400 is different from the configuration of the treatment device 1 of the first embodiment, in respect that the needle-like electrode portion 450 further includes an enlarged second electrode 452 which is provided to the outer surface of the distal end portion 11*a* of the sheath 11, in addition to the second electrode 52.

Figure 25:
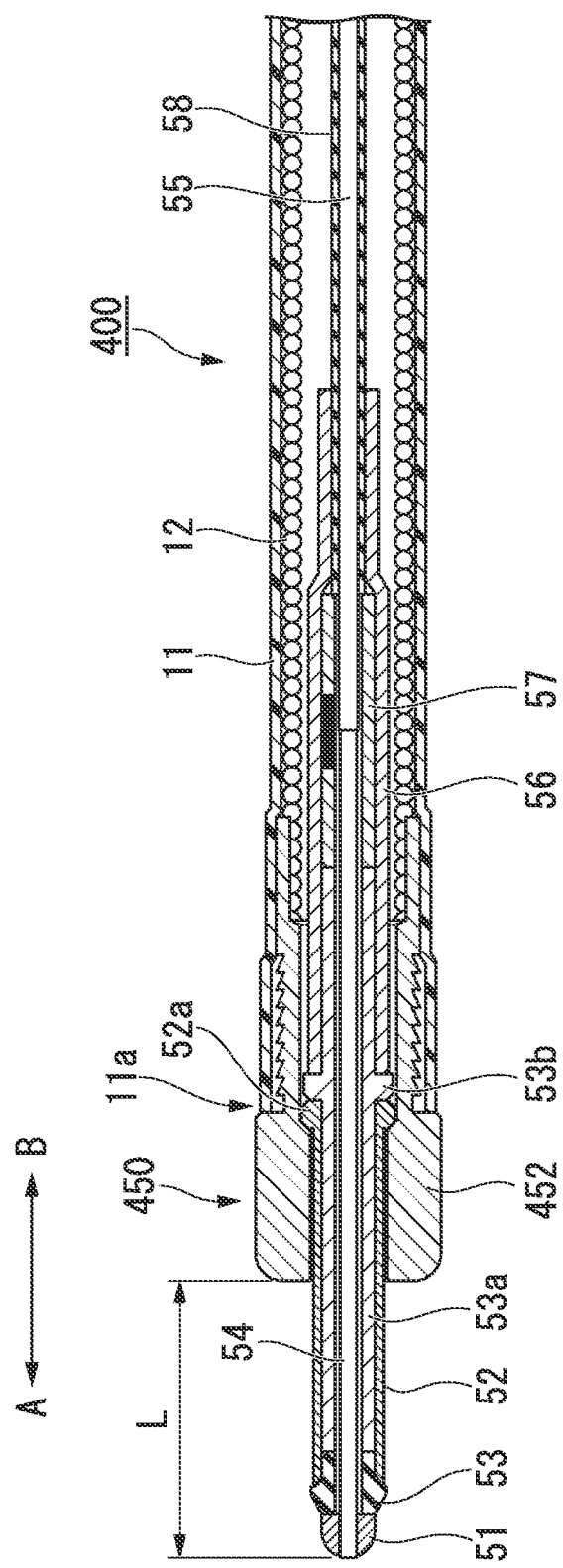
FIG. 25 is an enlarged cross-sectional view showing the configuration of a portion of the treatment device for electrosurgery.

FIG. 25 is a enlarged cross-sectional view showing the configuration of the distal end portion 11*a* of the sheath 11 in the treatment device 400. As shown in FIG. 25, the second electrode 52 is electrically connected to the enlarged second electrode 452, in the distal end portion 11*a* of the sheath 11. In addition, the enlarged second electrode 452 is integrally molded with the contact member 13. That is, the enlarged second electrode 452 is fixed and electrically connected to the coil sheath 12 similarly to the contact member 13 while functioning as the contact member 13.

In the treatment device 400, the second electrode 52 is conductive with the enlarged second electrode 452, so the second electrode 52 and the enlarged second electrode 452 function as a passive electrode with respect to the first electrode 51.

Figure 26:
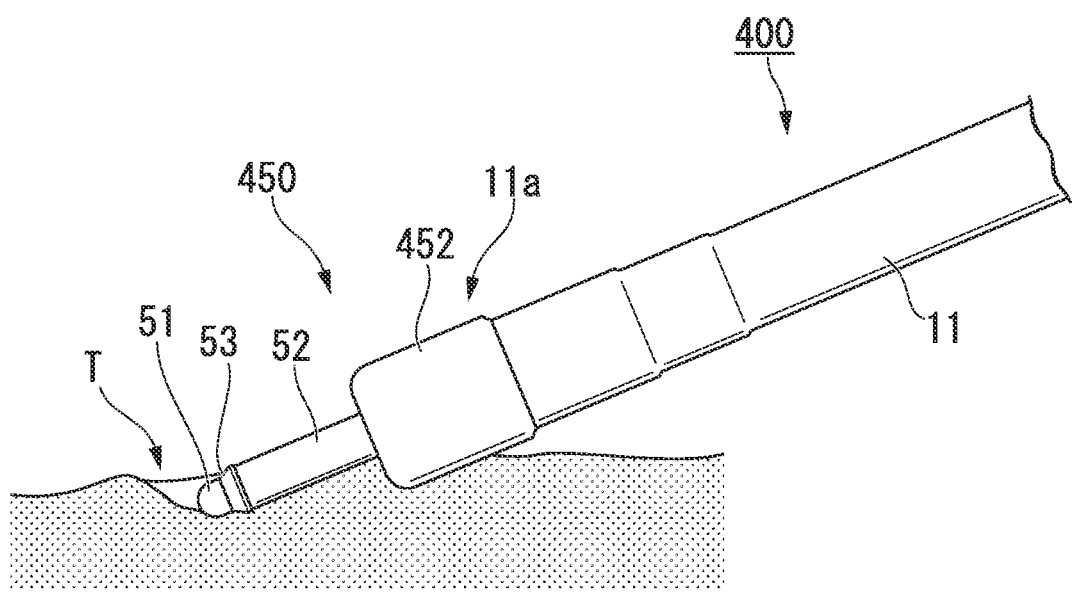
FIG. 26 is a view showing an operation performed when the treatment device for electrosurgery is used.

FIG. 26 is a view showing an operation at the time of using the treatment device 400. The treatment device 400 is guided into the body cavity similarly to the treatment device 1 of the first embodiment and further guided to a body tissue to be treated. In addition, by the operation of the user, the first electrode 51 and the second electrode 52 contacts the target site, similarly to the first embodiment. At this time, similarly to the treatment device 1 of the first embodiment, the user brings the first electrode 51 into contact with the target site, whereby the second electrode 52 also contacts the body tissue. Moreover, the enlarged second electrode 452 also contacts the body tissue.

In this state, by the operation of the user, the high-frequency current is applied between the first electrode 51 and the second electrode 52, and the high-frequency current is applied between the first electrode 51 and the enlarged second electrode 452. Accordingly, the body tissue that the first electrode 51 having a relatively small contact area with respect to the body tissue contacts is incised with cauterization.

As described above, according to the treatment device 400 of the present embodiment, since the enlarged second electrode 452 is provided in addition to the second electrode 52, the total surface area of the passive electrode that can contact the body tissue is large. In addition, even in a state where any of the second electrode 52 and the enlarged second electrode 452 is separated from the body tissue, the current is still applied between the first electrode 51 and the passive electrode. Accordingly, even when the user moves the first electrode 51 to a desired position, the user can continuously incise the body tissue suitably without caring about how the second electrode 52 and the enlarged second electrode 452 contact the body tissue.

Moreover, according to the treatment device 400 of the present embodiment, the enlarged second electrode 452 is provided to the sheath 11 having a relatively larger outer diameter compared to the first electrode. Accordingly, the enlarged second electrode 452 easily contacts the body tissue in the space of the target site T. As a result, it is possible to secure a sufficient contact area of the passive electrode with respect to the body tissue.

Figure 27:
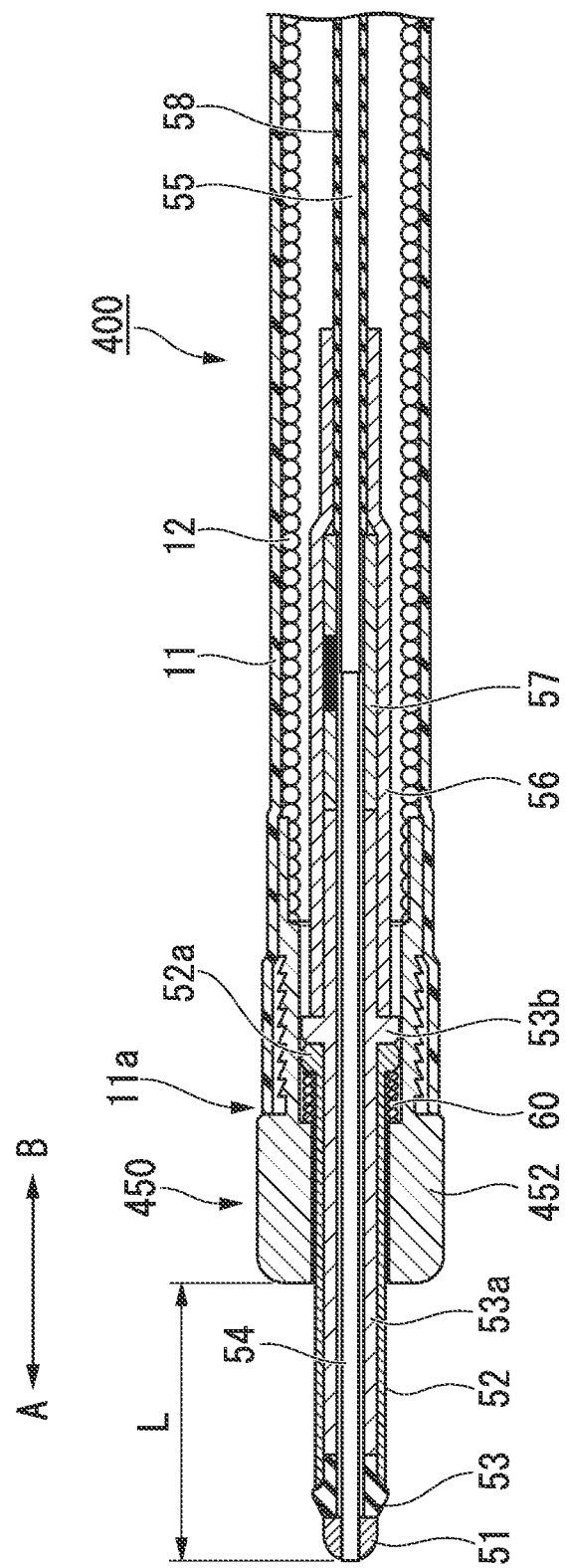
FIG. 27 is a cross-sectional view showing another configuration example of the treatment device for electrosurgery.

As shown in FIG. 27, in the present embodiment, the enlarged second electrode 452 may include the biasing member 60 described in Modified Example 3 of the first embodiment. In this case, even if the protruding amount by which the first electrode 51 protrudes from the sheath 11 is changed, and the positional relationship between the first electrode 51 and the enlarged second electrode 452 is changed, it is possible to apply the high-frequency current between the second electrode 52 as well as the enlarged second electrode 452 and the first electrode 51 via the target site T.

So far, the embodiments of the present invention have been described with reference to the drawings. However, the specific configuration is not limited to these embodiments and also includes the change of design within a range that does not depart from the scope of the present invention.

The configurations described in the above embodiments and modified examples can be employed by being appropriately combined.

The invention claimed is:

1. A treatment device for electrosurgery comprising:
a sheath which has a distal end portion and a proximal end portion;
a treatment portion which has a distal end and a proximal end, the treatment portion being inserted into the sheath such that a direction toward the distal end from the proximal end becomes a direction toward the distal end portion from the proximal end portion, wherein the treatment portion is configured to treat a target site by at least a portion of the distal end, and is capable of advancing and the treatment portion retracting inside the sheath;
a first electrode which is provided to the distal end of the treatment portion and exposed to the outside;
a second electrode of which the relative positional relationship with respect to the first electrode is fixed at a position separated from the first electrode toward the proximal end of the treatment portion;
an insulator which insulates the first electrode from the second electrode by being interposed between the first and second electrodes;
a first conductive portion which applies a high-frequency current to the first electrode;
a second conductive portion which applies a high-frequency current to the second electrode; and
a contact member which is fixed to the distal end portion of the sheath, which is electrically connected to the second conductive portion, and which is capable of being electrically connected to the second electrode, wherein
when the treatment portion protrudes from the sheath by a predetermined length, the second electrode is electrically connected to the second conductive portion via the contact member, and
the second electrode is not electrically connected to the second conductive portion via the contact member when the treatment portion protrudes from the sheath at a length that is less than the predetermined length.

2. The treatment device for electrosurgery according to claim 1, wherein the first electrode is formed while bulging to the outside in the radial direction of the treatment portion so as to have a diameter greater than or equal to an external diameter of the second electrode.

3. The treatment device for electrosurgery according to Claim 2, wherein the first electrode is formed in a semispherical shape of which the diameter decreases toward the distal end from the proximal end.

4. The treatment device for electrosurgery according to claim 3, wherein a distal end of the second electrode comprises an extending portion that is integrally formed therewith, wherein the extending portion extends to the outside in the radial direction.

5. The treatment device for electrosurgery according to claim 1, wherein the sheath includes an electroconductive coil sheath in the inside thereof, and the coil sheath functions as a portion of the second conductive portion.

6. The treatment device for electrosurgery according to claim 1, further comprising:
a second insulator which hides at least a portion of the outer surface of the second electrode so as to expose a portion of a distal end of the second electrode having approximately a same area as a surface area of the first electrode.

7. The treatment device for electrosurgery according to claim 1, wherein the first electrode is a portion of a ring-like snare loop having electrical conductivity.

8. The treatment device for electrosurgery according to claim 1, wherein the first electrode is a pair of two-legged forceps having a pair of elastic gripping portions that extend in the distal end direction from the proximal end and can be opened and closed using the proximal end as a center of opening and closing.

* * * * *